United States Patent
Mukherjee et al.

(10) Patent No.: US 9,629,816 B2
(45) Date of Patent: Apr. 25, 2017

(54) SMALL MOLECULE THERAPEUTIC COMPOUNDS TARGETING THIOESTERASE DEFICIENCY DISORDERS AND METHODS OF USING THE SAME

(75) Inventors: Anil Baran Mukherjee, Brookeville, MD (US); Chinmoy Sarkar, Rockville, MD (US); Zhongjian Zhang, Rockville, MD (US)

(73) Assignee: The United States of America, as represented by the Secretary, Dept. of Health and Human Services, Washington, DC (US)

( * ) Notice: Subject to any disclaimer, the term of this patent is extended or adjusted under 35 U.S.C. 154(b) by 606 days.

(21) Appl. No.: 14/110,393

(22) PCT Filed: Apr. 9, 2012

(86) PCT No.: PCT/US2012/032772
§ 371 (c)(1),
(2), (4) Date: Feb. 5, 2014

(87) PCT Pub. No.: WO2012/139119
PCT Pub. Date: Oct. 11, 2012

(65) Prior Publication Data
US 2014/0148513 A1    May 29, 2014

Related U.S. Application Data

(60) Provisional application No. 61/473,692, filed on Apr. 8, 2011.

(51) Int. Cl.
| | |
|---|---|
| *A61K 31/13* | (2006.01) |
| *A61K 31/133* | (2006.01) |
| *A61K 31/00* | (2006.01) |
| *A61K 31/136* | (2006.01) |
| *A61K 31/137* | (2006.01) |
| *A61K 45/06* | (2006.01) |

(52) U.S. Cl.
CPC ............ *A61K 31/133* (2013.01); *A61K 31/00* (2013.01); *A61K 31/136* (2013.01); *A61K 31/137* (2013.01); *A61K 45/06* (2013.01)

(58) Field of Classification Search
CPC .............................. A61K 31/13; A61K 31/133
USPC ........................................................ 514/645
See application file for complete search history.

(56) References Cited

U.S. PATENT DOCUMENTS

2006/0147431 A1    7/2006 Uchida et al.
2009/0047250 A1*   2/2009 Elford .................. A61K 31/133
                                                            424/85.6

OTHER PUBLICATIONS

International Search Report and Written Opinion prepared by the European Patent Office on Jun. 19, 2012, for International Application No. PCT/US2012/032772.
Kim et al. "Palmitoyl protein thioesterase-1 deficiency impairs synaptic versicle recycling at nerve terminals, contributing to neuropathyology in humans and mice." The Journal of Clinical Investigation, vol. 118, No. 9, 2008, pp. 2075-2086.
Michela et al. "Glycoproteomics of paclitaxel resistance in human epithelial ovarian cancer cell lines: towards the identification of putative biomarkers." Journal of Proteomics, vol. 73, 2010, pp. 879-898.

* cited by examiner

*Primary Examiner* — Kevin E Weddington
(74) *Attorney, Agent, or Firm* — Sheridan Ross P.C.

(57) ABSTRACT

The invention provides methods of inhibiting the development or progression of a thioesterase deficiency disorder in a mammal by the administration of a compound that functionally mimics the enzymatic activity of all thioesterases in mammals. Such thioesterase deficiency disorders include cancers and adult- or infant-neuronal ceroid lipofuscinoses (NCLs). The invention also provides small molecule mimics of thioesterases useful in the methods of the invention and pharmaceutical compositions containing the therapeutically effective compounds and methods of using the same.

7 Claims, 11 Drawing Sheets

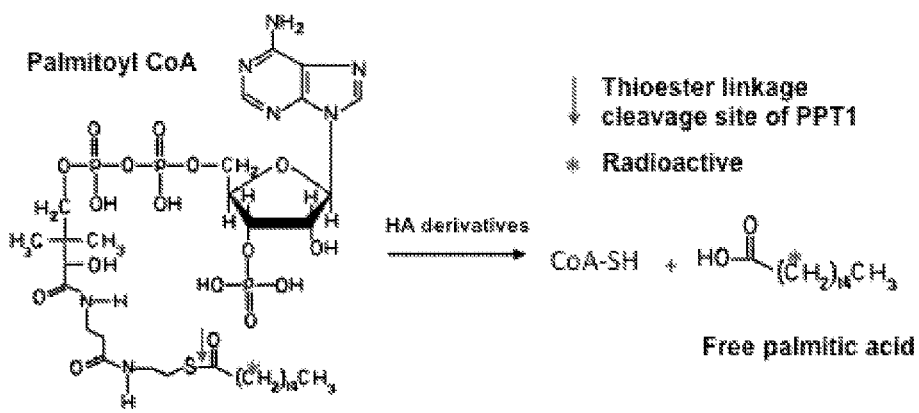
Figure 2
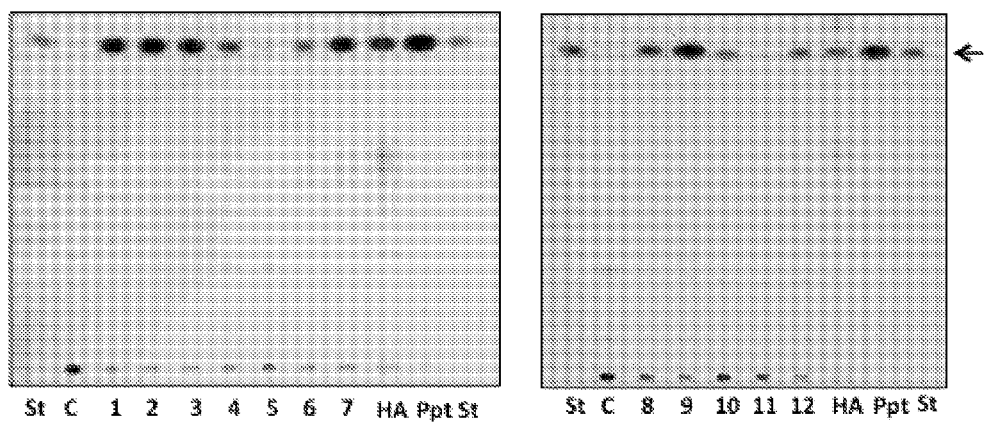
Figure 3
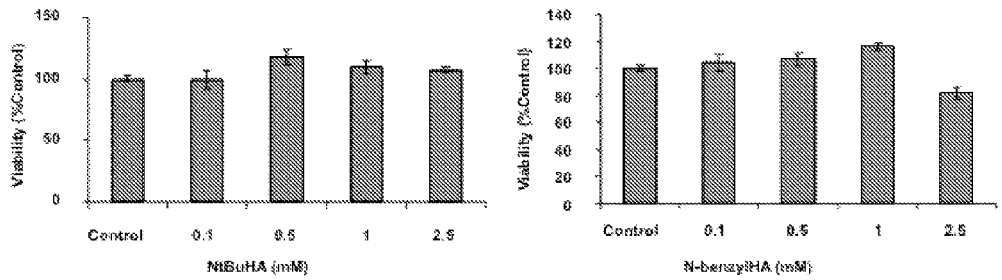
Figure 4 – A

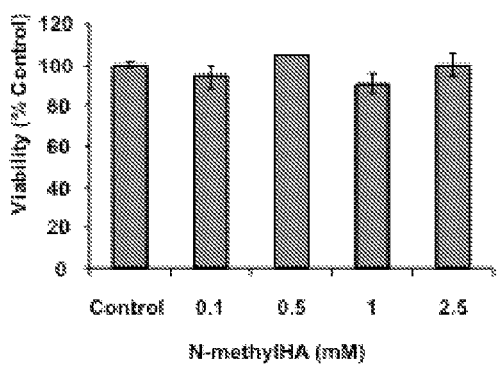
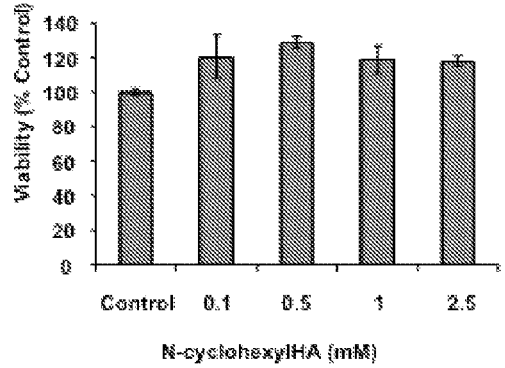
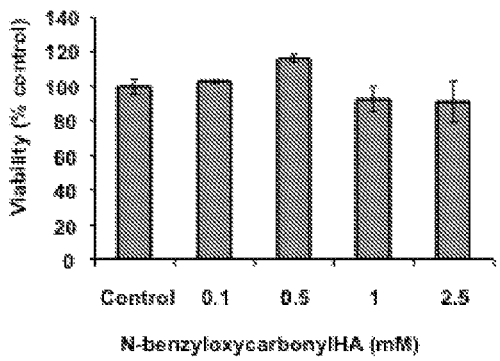
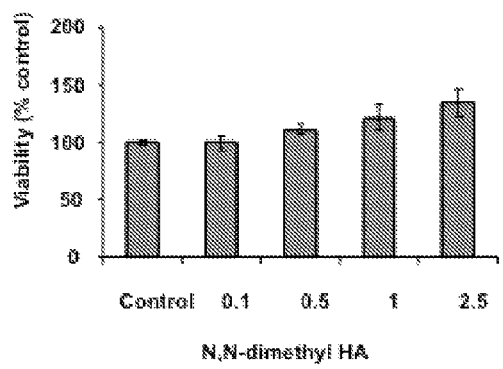
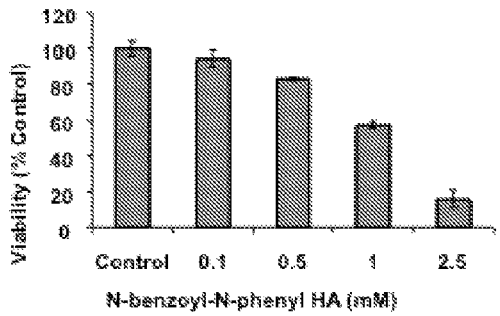
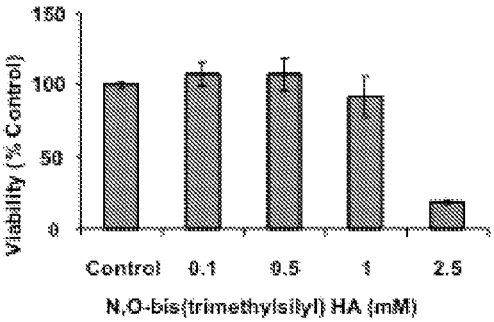
Figure 4 – B

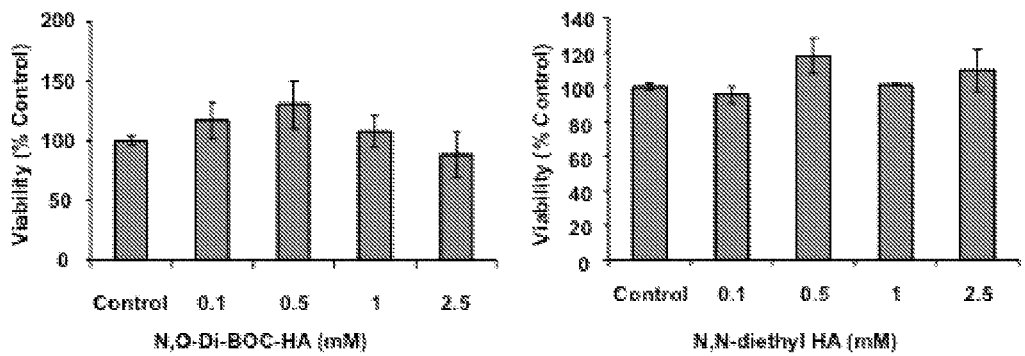
Figure 4 – C
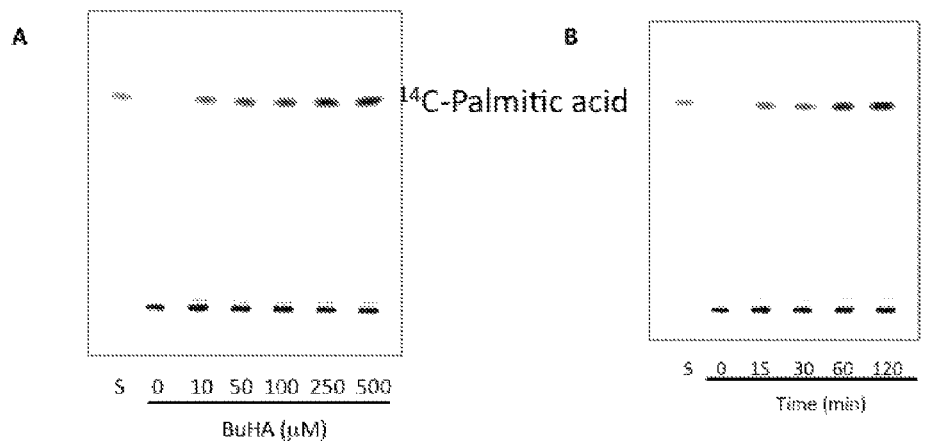
Figure 5
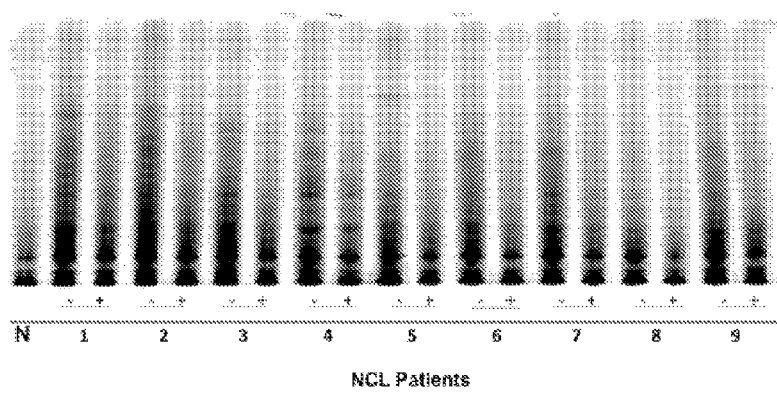
Figure 8

SMALL MOLECULE THERAPEUTIC COMPOUNDS TARGETING THIOESTERASE DEFICIENCY DISORDERS AND METHODS OF USING THE SAME

CROSS REFERENCE TO RELATED APPLICATIONS

This application is a national stage application under 35 U.S.C. 371 and claims the benefit of PCT Application No. PCT/US2012/032772 having an international filing date of 9 Apr. 2012, which designated the United States, and which PCT application claimed the benefit of U.S. Provisional Application No. 61/473,692 filed on 8 Apr. 2011, the entire disclosure of each is incorporated by reference herein.

TECHNICAL FIELD

The invention relates to therapeutic compounds, pharmaceutical compositions containing these compounds, and their use in the prevention or treatment of diseases resulting from thioesterase deficiency disorders.

BACKGROUND OF INVENTION

Lysosomal storage disorders represent a group of at least 50 genetically distinct, biochemically related, inherited diseases. Individually, these disorders are considered rare, although high prevalence values have been reported in some populations. These disorders are devastating for individuals and their families and result in considerable use of resources from health care systems, however, the magnitude of the problem is not well defined. Included amongst these lysosomal storage disorders are mutations or other disruptions of thioesterases, which result in the accumulation of posttranslationally lipid-modified proteins in lysosomes.

Thioesterases are enzymes in the esterase family (members of E.C.3.1.2), which split an ester (specifically at a thiol group) into an acid and alcohol, in the presence of water. Examples of human thioesterases include acetyl-coA hydrolase, palmitoyl-CoA hydrolase, succinyl-CoA hydrolase, formyl-CoA hydrolase, acyl-CoA hydrolase, and ubiquitin thiolesterase and human genes encoding thiol esterases include: ACOT1, ACOT2, ACOT4, ACOT6, ACOT7, ACOT8, ACOT9, ACOT11 (STARD14), ACOT12 (STARD15), OLAH, APT1, APT2, PPT1, PPT2, THEM2 (ACOT13), THEM4, THEM4P1, and THEM5.

An example of a lysosomal storage disorder resulting from one or more mutations in a thioesterase is infantile neuronal ceroid lipofuscinosis (INCL), which is a lethal childhood neurodegenerative storage disorder caused by palmitoyl protein thioesterase-1 (PPT1) gene mutations. Palmitoylation is a posttranslational modification in which a 16-carbon fatty acid, palmitate, is attached to specific cysteine residues in polypeptides via thioester linkage. PPT1 cleaves thioester linkages in S-acylated proteins facilitating degradation or recycling and its deficiency leads to lysosomal storage of these proteins causing INCL pathogenesis, as depicted in FIG. 1. Currently, there is no effective treatment for INCL.

As an example of cancers associated with thioesterase deficiencies, Ras is mutated in cancer more frequently than any other oncogene. Hence, Ras has been a focus for the development of rationally designed anti-cancer drugs, yet to date none have been successfully developed. Posttranslational lipid-modification of Ras proteins is essential for Ras membrane association and transformation. The differences in the four Ras isoforms, N-Ras, H-Ras, K-Ras4A and KRas4B reside in the C-terminal region referred to as the hypervariable region (HVR), which is modified by post-translational lipid-modifications. H-Ras is modified by two cysteine palmitoylations and one cysteine farnesylation, whereas N-Ras and K-Ras(A) are modified by one cysteine palmitoylation and one cysteine farnesylation. In contrast, K-Ras(B) is not palmitoylated. Reversible palmitoylations of H- and N-Ras GTPases control their membrane attachment and specific localization on the plasma membrane and the Golgi. Proper steady state localization requires a dynamic cycle of palmitoylation on the Golgi, which redirects Ras to the plasma membrane, and ubiquitous depalmitoylation to counteract spontaneous nonspecific distribution over cellular endo membranes. Disruption of this dynamic cycle results in a reduction of Ras localization on the Golgi and the plasma membrane, due to random redistribution to endo membranes, indicating that inhibitors of palmitoylation as well as enzymatic depalmitoylation alter the steady state localization of Ras GTPases and thus Ras signaling.

Thus, thioesterases present a compelling therapeutic target for the prevention and treatment of thioesterase deficiency disorders such as lysosomal storage disorders including INCL, and cancers associated with Ras localization and activation, and there exists a need for effective methods of inhibiting Ras GTPases for the treatment and prevention of these thioesterase deficiency disorders.

SUMMARY OF INVENTION

The present invention provides small molecules that functionally mimic thioesterase activity, as well as therapeutic uses of these molecules to prevent or treat neurodegenerative disorders or slow the growth and metastasis of cancers resulting from a thioesterase deficiency in a mammal.

Despite the fact that hydroxylamine (HA) specifically cleaves thioester linkages in S-acylated proteins, HA-mediated methemoglobin production causes toxicity because methemoglobin cannot carry oxygen like hemoglobin does. Thus, toxicity of HA precludes its clinical use. However, HA-derivatives may be non-toxic. The present inventors have screened 12 HA-derivatives for their ability to cleave thioester linkages like the parent compound, HA and discovered that they do indeed have this property. (See Table 1 for a listing of these HA-derivatives). They found that one of these HA-derivatives, N-t-butyl hydroxylamine (Nt-BuHA), is non-toxic to both cultured cells from INCL patients and to Ppt1-Knockout (Ppt1-KO) mice, which recapitulate virtually all clinical and pathological features of INCL. It also does not cause elevated levels of methemoglobin. (See Table 3). Moreover, it has potent antioxidant properties, cleaves thioester linkage in S-acylated proteins and reduces intracellular ceroid load in cultured INCL cells. Additional animal studies showed that dietary NtBuHA showed no toxicity, depleted lysosomal ceroid, reduced endoplasmic reticulum- and oxidative-stresses, suppressed apoptosis, improved neurological function, and markedly extended lifespan in Ppt1-KO mice, which mimic INCL, as compared to their untreated littermates, demonstrating that NtBuHA may be used in the treatment of thioesterase deficiency disorders such as INCL.

Therefore, the present invention provides compounds that functionally mimic thioesterase activity in mammals having a thioesterase deficiency, and pharmaceutically-acceptable salts and prodrugs thereof. The invention also provides pharmaceutical compositions containing these compounds.

The invention also provides methods of using these compounds and pharmaceutical compositions to treat or prevent thioesterase deficiency disorders in a mammal in need of, or suspected of needing, such treatment.

One embodiment of the invention is a method of treating a thioesterase deficiency disorder by administering to a mammal in need of such treatment, a therapeutically effective amount of a compound that functionally mimics thioesterase enzymatic activity. In one aspect of this embodiment, the compound mimics palmitoyl-protein thioesterase-1 (PPT1), thereby treating PPT1-deficiency or preventing abnormal lysosomal ceroid accumulation responsible for PPT 1-deficiency. In another aspect of the invention, the compound mimics all thioesterases thereby treating cancers associated with the deficiencies of these thioesterases and preventing the growth and metastasis of these tumors.

In a preferred embodiment of these aspects of the invention, the compound is at least one of the compounds of Table 1.

In a preferred embodiment, the compound is administered to the mammal in a pharmaceutical composition of the invention. In a particularly preferred embodiment of the invention, the compound administered is N-t-butyl hydroxylamine (NtBUHA).

Additionally, the invention provides pharmaceutical compositions containing one or more of the compounds of Table 1, or pharmaceutically-acceptable salts thereof, with at least one pharmaceutically-acceptable carrier. Also provided herein is a pharmaceutical composition comprising at least one prodrug of at least one compound of the invention, with at least one pharmaceutically acceptable carrier.

Another embodiment of the invention is a method of preventing or treating cancers associated with thioesterase deficiencies, by administering a therapeutically effective amount of one of the compounds of the invention, or a pharmaceutically acceptable salt thereof, or prodrug thereof, to a mammal in need of such treatment or suspected of having a thioesterase deficiency related cancer or a metastasis of a thioesterase deficiency related cancer.

Another embodiment of the invention is a method of preventing or treating neurodegenerative disorders associated with thioesterase deficiencies, by administering a therapeutically effective amount of one of the compounds of the invention, or a pharmaceutically acceptable salt thereof, or prodrug thereof, to a mammal in need of such treatment or suspected of having a neurodegenerative disorder associated with a thioesterase deficiency disorder. In a related embodiment, the invention is a method of preventing or treating infantile NCL (INCL) caused by palmitoyl-protein thioesterase-1 (PPT 1)-deficiency.

Another embodiment of this invention is a method of treating cancer by administering a therapeutically effective combination of at least one of the compounds of Table 1 and one or more other known anti-cancer or anti-inflammatory treatments. For example, other anti-cancer treatments may include surgery, chemotherapy, radiation, immunotherapy, or combinations thereof.

Also provided herein are methods for the prevention, treatment or prophylaxis of neurodegeneration in a mammal secondary to lysosomal storage disorders including, but not limited to, neuronal ceroid lipofuscinoses (NCLs; also known as Batten disease) and infantile NCL (INCL; also known as infantile Batten disease). These methods comprise administering to a mammal in need of such treatment, therapeutically-effective amounts of any of the compounds of Table 1, pharmaceutical compositions of the invention containing at least one of the compounds of Table 1, and/or pharmaceutical compositions comprising at least one prodrug of the compounds of Table 1.

Also provided herein are methods for preventing at least one symptom of lysosomal storage disorders in a mammal including, but not limited to, psychomotor retardation, retinal blindness, myoclonus, seizures, intracellular autofluorescent storage material and reduced lifespan. These methods comprise administering to a mammal suspected of having a lysosomal storage disorder therapeutically-effective amounts of any of the compounds of Table 1, pharmaceutical compositions of the invention containing at least one of the compounds of Table 1, and/or pharmaceutical compositions comprising at least one prodrug of the compounds of Table 1, prior to the development of a symptom of a lysosomal storage disorder.

Also provided herein are pharmaceutical packages comprising a pharmaceutical composition comprising therapeutically-effective amounts of at least one compound of Table 1, optionally together with at least one pharmaceutically acceptable carrier. The pharmaceutical compositions may be administered separately, simultaneously or sequentially, with other compounds or therapies used in the prevention, treatment or amelioration of thioesterase deficiency-related cancers and/or neurodegenerative disorders. These packages may also include prescribing information and/or a container. If present, the prescribing information may describe the administration, and/or use of these pharmaceutical compositions alone or in combination with other therapies used in the prevention, treatment or amelioration of thioesterase deficiency-related cancers and/or neurodegenerative disorders.

Also provided herein are pharmaceutical packages containing a pharmaceutical composition of at least one prodrug of a compound of Table 1, optionally together with at least one pharmaceutically-acceptable carrier. These packages may also include prescribing information and/or a container. If present, the prescribing information may describe the administration, and/or use of these pharmaceutical compositions alone or in combination with other therapies used in the prevention, treatment or amelioration of thioesterase deficiency-related cancers and/or neurodegenerative disorders.

Another embodiment of this invention is a method of testing the susceptibility of a mammal having a thioesterase deficiency-related cancer and/or neurodegenerative disorder to treatment with a putative mimic of thioesterase activity by testing the mammal for a response to the putative mimic, wherein the response is indicative of growth inhibition or reduction in cancer cell number or neurodegenerative disorders in the mammal.

Other aspects of the invention will be set forth in the accompanying description of embodiments, which follows and will be apparent from the description or may be learnt by the practice of the invention. However, it should be understood that the following description of embodiments is given by way of illustration only since various changes and modifications within the spirit and scope of the invention will become apparent to those skilled in the art and are encompassed within the scope of this invention.

BRIEF DESCRIPTION OF DRAWINGS

FIG. 2 depicts the screening method utilized to test HA-derivatives for their ability to cleave thioester linkage in [$^{14}$C]palmitoyl~CoA (a model thioester substrate of PPT1).

FIG. 3 depicts the densitometric analysis of the free [$^{14}$C]-palmitate bands for twelve HA-derivatives that were screened for their ability to cleave thioester linkage in [$^{14}$C]palmitoyl~CoA.

FIG. 4A-C charts the results of an MTT assay determining the viability, as a percentage of untreated control, of INCL fibroblasts following 48 hours of treatment with ten HA-derivatives: N-t-butyl hydroxylamine (NtBuHA), N-benzyl-hydroxylamine, N-Methyl hydroxylamine, N-cyclohexyl hydroxylamine, N-benzyloxycarbonyl hydroxylamine, N,N-dimethyl hydroxylamine, N,N-diethyl hydroxylamine, N-benzoyl-N-phenyl hydroxylamine, (i) N,O-bis(trimethyl-silyl)hydroxylamine, and N,O-Di-BOC hydroxylamine.

FIG. 5A-B depicts the thioester linkages of NtBuHA-treated INCL cells in a dose-dependent (5A) and time-dependent (5B) manner.

FIG. 8 depicts the densitometric analysis of [$^{35}$S]cysteine-labeled lipid bands for both untreated- (labeled "−") and NtBuHA-treated (labeled "+") lympohblasts in the cell lines of nine NCL patients.

FIG. 18D charts the quantitative results of this analysis by number of NeuN-positive cells, wherein "1" represents cortical tissues from wild-type mice, "2" represents cortical tissues from untreated-PPT 1-KO mice, and "3" represents cortical tissues NtBuHA-treated PPT 1-KO mice.

DETAILED DESCRIPTION OF EMBODIMENTS

Figure 1:
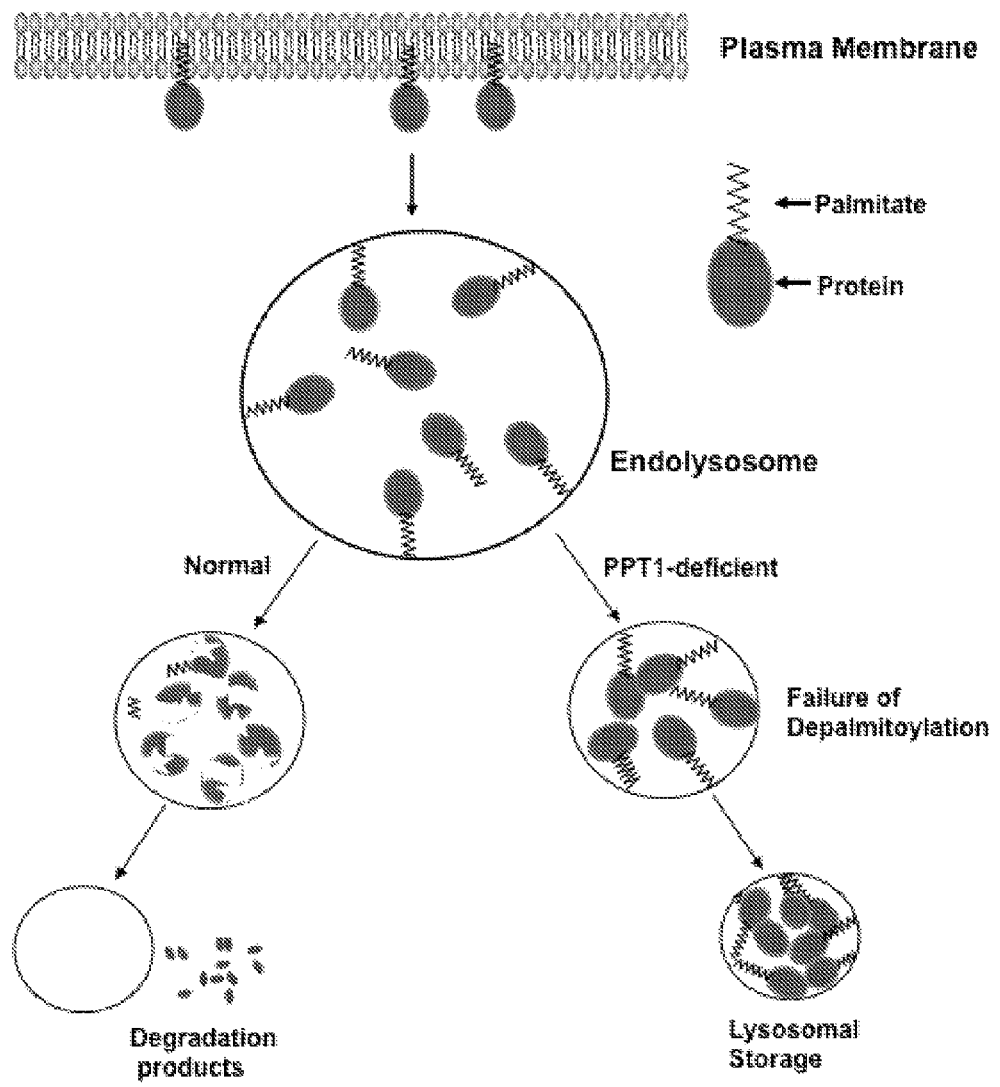
FIG. 1 models the suggested mechanism of lysosomal storage in PPT1-deficient cells versus normal cells.

Based on their compelling clinical significance in cancer and neurodegeneration, the present inventors have identified and used thioesterases as molecular targets. The thioester linkage is labile and nucleophilic attack readily disrupts this linkage. The present inventors therefore reasoned that pharmacological agents with nucleophilic properties might have a therapeutic potential for the treatment of thioesterase deficiency disorders by mimicking thioesterase activity. To develop a therapeutic strategy for such thioesterase deficiency disorders with small molecules, the present inventors rationalized that for a compound to be a potential drug candidate it must satisfy at least three criteria:

1) It must be non-toxic,
2) It must be a compound with nucleophilic properties, and
3) It must cross the blood-brain barrier.

Hydroxylamine (HA) is a small molecule with nucleophilic activity and it cleaves thioester linkages with high specificity and thus, functionally mimics thioesterase activity, especially PPT1 activity. Unfortunately, HA toxicity precludes its clinical use for any disorder. For this reason, the present inventors examined some non-toxic derivatives of HA for indications of anti-oxidant properties and the ability of these compounds to cleave thioester linkages in s-acylated proteins and to facilitate the depletion of ceroid in cell and animal models. The HA-derivatives of Table 1 were determined to be non-toxic and able to cleave thioester linkages in [$^{14}$C]-palmitoyl~CoA, a model high-energy thioester substrate of PPT1. Additionally, the present inventors demonstrated that each of the HA-derivatives of Table 1 hydrolyze the thioester linkage in [$^{14}$C]-palmitoyl~CoA as well as in s-acylated proteins from cultured INCL lymphoblasts in a dose- and time-dependent manner.

In one aspect, the invention is a method of inhibiting the development of neurodegenerative disorders or the growth and/or metastasis of cancer in a mammal by administering at least one compound of Table 1, or pharmaceutically-acceptable salts and/or prodrugs thereof to the mammal.

TABLE 1

Compounds screened for thioesterase-like activity in the present invention

| | Chemical Formula | Description |
|---|---|---|
| 1. | $NH_2OH$ | Hydroxylamine |
| 2. | $CH_5NO$ | N-Methylhydroxylamine |
| 3. | $C_2H_7NO$ | N,N-Dimethylhydroxylamine |
| 4. | $C_4H_{11}NO$ | N,N-Diethylhydroxylamine |
| 5. | $C_6H_{13}NO$ | N-Cyclohexylhydroxylamine |
| 6. | $C_6H_{15}NO_3$ | N-(tert-Butyl)hydroxylamine |
| 7. | $C_6H_{19}NOSi_2$ | N,O-Bis(trimethylsilyl) hydroxylamine |
| 8. | $C_7H_9NO$ | N-Benzylhydroxylamine |
| 9. | $C_8H_9NO_3$ | N-Benzyloxycarbonyl) |
| 10. | $C_{10}H_{19}NO_5$ | N,O-Di-Boc-hydroxylamine |
| 11. | $C_{13}H_{11}NO_2$ | N-Benzoyl-N-phenyl hydroxylamine |
| 12. | $C_{14}H_{15}NO$ | N,N-Dibenzylhydroxylamine |
| 13. | $C_{23}H_{32}ClNO$ | N-tert-Butyl-O-[1-[4-(chloromethyl) phenyl]ethyl]-N-(2-methyl-1-phenylpropyl) hydroxylamine |

As used herein, the term "compound" means a chemical or biological molecule such as a simple or complex organic molecule, a peptide, a protein or an oligonucleotide. Exemplary therapeutic compounds of the invention are those compounds listed in Table 1 of this disclosure.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

"Pharmaceutically-acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, or alkali or organic salts of acidic residues such as carboxylic acids. Pharmaceutically-acceptable salts include the conventional non-toxic salts or the quaternary ammonium salts of the parent compound formed, for example, from non-toxic inorganic or organic acids. Such conventional nontoxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Pharmaceutically acceptable salts are those forms of compounds, suitable for use in contact with the tissues of human beings and animals without excessive toxicity, irritation, allergic response, or other problem or complication, commensurate with a reasonable benefit/risk ratio.

Pharmaceutically-acceptable salt forms of compounds provided herein are synthesized from the compounds of Table 1 that contain a basic or acidic moiety by conventional chemical methods. Generally, such salts are, for example, prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in at page 1418 of Remington's Pharmaceutical Sciences, 17th ed., Mack Publishing Company, Easton, Pa., 1985.

"Prodrugs" are intended to include any covalently bonded carriers that release an active parent drug of the present invention in vivo when such prodrug is administered to a mammalian subject. Since prodrugs are known to enhance numerous desirable qualities of pharmaceuticals (i.e., solubility, bioavailability, half life, manufacturing, etc.) the compounds of the present invention may be delivered in prodrug form. Thus, the present invention is intended to cover prodrugs of the presently claimed compounds, methods of delivering the same, and compositions containing the same. Prodrugs of the present invention are prepared by modifying functional groups present in the compound in such a way that the modifications are cleaved, either in routine manipulation or in vivo, to a compound of the invention. Prodrugs include compounds of the present invention wherein an acyl, hydroxy, amino, or sulfhydryl group is bonded to any group that, when the prodrug of the present invention is administered to a mammalian subject, is cleaved to form a free acetyl, hydroxyl, free amino, or free sulfhydryl group, respectively. Examples of prodrugs include, but are not limited to, acetate, formate, and benzoate derivatives of alcohol and amine functional groups in the compounds of the present invention.

The term "therapeutically-effective amount" of a compound of this invention means an amount effective to inhibit the formation or progression of a thioesterase deficiency disorder following administration to a mammal having a thioesterase deficiency disorder.

It will be appreciated by those skilled in the art that compounds of the invention having a chiral center may exist in, and may be isolated in, optically active and racemic forms. It is to be understood that the compounds of the present invention encompasses any racemic, optically-active, regioisomeric or stereoisomeric form, or mixtures thereof, which possess the therapeutically useful properties described herein. It is well known in the art how to prepare optically active forms (for example, by resolution of the racemic form by recrystallization techniques, by synthesis from optically-active starting materials, by chiral synthesis, or by chromatographic separation using a chiral stationary phase). It is also to be understood that the scope of this invention encompasses not only the various isomers, which may exist but also the various mixtures of isomers, which may be formed. For example, if the compound of the present invention contains one or more chiral centers, the compound can be synthesized enantioselectively or a mixture of enantiomers and/or diastereomers can be prepared and separated. The resolution of the compounds of the present invention, their starting materials and/or the intermediates may be carried out by known procedures, e.g., as described in the four volume compendium Optical Resolution Procedures for Chemical Compounds: Optical Resolution Information Center, Manhattan College, Riverdale, N.Y., and in Enantiomers, Racemates and Resolutions, Jean Jacques, Andre Collet and Samuel H. Wilen; John Wiley & Sons, Inc., New York, 1981, which is incorporated in its entirety by this reference. Basically, the resolution of the compounds is based on the differences in the physical properties of diastereomers by attachment, either chemically or enzymatically, of an enantiomerically pure moiety resulting in forms that are separable by fractional crystallization, distillation or chromatography.

The compounds used in making the pharmaceutical compositions of the present invention may be purchased commercially. The compounds of the present invention, including the salts and prodrugs of these compounds, may also be prepared in ways well known to those skilled in the art of organic synthesis. The compounds of the invention may be prepared using the reactions performed in solvents appropriate to the reagents and materials employed and suitable for the transformation being effected. It is understood by one skilled in the art of organic synthesis that the functionality present on various portions of the molecule must be compatible with the reagents and reactions proposed. Such restrictions to the substituents, which are compatible with the reaction conditions, will be readily apparent to one skilled in the art and alternate methods must then be used.

Also provided herein are pharmaceutical compositions containing compounds of the invention and a pharmaceutically-acceptable carrier, which are media generally accepted in the art for the delivery of biologically active agents to animals, in particular, mammals. Pharmaceutically-acceptable carriers are formulated according to a number of factors well within the purview of those of ordinary skill in the art to determine and accommodate. These include, without limitation: the type and nature of the active agent being formulated; the subject to which the agent-containing composition is to be administered; the intended route of administration of the composition; and, the therapeutic indication being targeted. Pharmaceutically-acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically-acceptable carriers, and factors involved in their selection, are found in a variety of readily available sources, such as Remington's Pharmaceutical Sciences, 17th ed., Mack Publishing Company, Easton, Pa., 1985.

This invention further provides a method of treating a mammal afflicted with a thioesterase deficiency disorder or preventing the development of such thioesterase deficiency disorder in a mammal, which includes administering to the mammal a pharmaceutical composition provided herein. Such compositions generally comprise a therapeutically effective amount of a compound of Table 1 in an amount effective to prevent, ameliorate, lessen or inhibit the thioesterase deficiency disorder. Such amounts typically comprise from about 0.1 to about 100 mg of the compound per kilogram of body weight of the mammal to which the composition is administered. Therapeutically effective amounts can be administered according to any dosing regimen satisfactory to those of ordinary skill in the art.

Administration may be, for example, by various parenteral means. Pharmaceutical compositions suitable for parenteral administration include various aqueous media such as aqueous dextrose and saline solutions; glycol solutions are also useful carriers, and preferably contain a water soluble salt of the active ingredient, suitable stabilizing agents, and if necessary, buffering agents. Antioxidizing agents, such as sodium bisulfite, sodium sulfite, or ascorbic acid, either alone or in combination, are suitable stabilizing agents; also used are citric acid and its salts, and EDTA. In addition, parenteral solutions can contain preservatives such as benzalkonium chloride, methyl- or propyl-paraben, and chlorobutanol.

Alternatively, compositions can be administered orally in solid dosage forms, such as capsules, tablets and powders; or in liquid forms such as elixirs, syrups, and/or suspensions. Gelatin capsules can be used to contain the active ingredient and a suitable carrier such as, but not limited to, lactose, starch, magnesium stearate, stearic acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

A preferred formulation of the invention is a mono-phasic pharmaceutical composition suitable for parenteral or oral administration for the prevention, treatment or prophylaxis of a thioesterase deficiency disorder, consisting essentially of a therapeutically-effective amount of a compound of the invention, and a pharmaceutically acceptable carrier.

Another preferred formulation of the invention is a mono-phasic pharmaceutical composition suitable for the prevention, treatment or prophylaxis of a thioesterase deficiency disorder, consisting essentially of a therapeutically-effective amount of a prodrug of a compound of the invention, and a pharmaceutically acceptable carrier.

Examples of suitable aqueous and nonaqueous carriers that may be employed in pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents that delay absorption such as aluminum monosterate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn may depend upon crystal size and crystalline form. Alternatively, delayed absorption of a parenterally-administered drug is accomplished by dissolving or suspending the drug in an oil vehicle.

Injectable depot forms are made by forming microencapsulated matrices of the drug in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue. The injectable materials can be sterilized for example, by filtration through a bacterial-retaining filter.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the therapeutic compounds of the present invention.

Formulations of the invention suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of a compound or compounds of the present invention as an active ingredient. A compound or compounds of the present invention may also be administered as bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monosterate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may be employed as fillers in soft and hard-filled gelatin capsules using such excipients as lactose or milk sugars, as well as high molecular weight polyethylene glycols and the like.

A tablet may be made by compression or molding optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient only, or preferentially, in a certain portion of the gastrointestinal tract, optionally, in a delayed manner. Examples of embedding compositions that can be used include polymeric substances and waxes. The active ingredient can also be in microencapsulated form.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Liquid dosage forms for oral administration of the compounds of the invention include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or salicylate, and which is solid at room temperature, but liquid at body temperature and, therefore, will melt in the rectum or vaginal cavity and release the active compound. Formulations of the present invention which are suitable for vaginal administration also include pessaries, tampons, creams, gels, pastes, foams or spray formulations containing such carriers as are known in the art to be appropriate.

Dosage forms for the topical or transdermal administration of compounds of this invention include powders, sprays, ointments, pastes, creams, lotions, gels, solutions, patches, drops and inhalants. The active ingredient may be mixed under sterile conditions with a pharmaceutically-acceptable carrier, and with any buffers, or propellants that may be required.

The ointments, pastes, creams and gels may contain, in addition to an active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active ingredient, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane.

Transdermal patches have the added advantage of providing controlled delivery of compounds of the invention to the body. Such dosage forms can be made by dissolving, dispersing or otherwise incorporating one or more compounds of the invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Pharmaceutical formulations include those suitable for administration by inhalation or insufflation or for nasal or intraocular administration. For administration to the upper (nasal) or lower respiratory tract by inhalation, the compounds of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of one or more of the anti-cancer compounds of the invention and a suitable powder base, such as lactose or starch. The powder composition may be presented in unit dosage form in, for example, capsules or cartridges, or, e.g., gelatin or blister packs from which the powder may be administered with the aid of an inhalator, insufflator or a metered-dose inhaler.

For intranasal administration, compounds of the invention may be administered by means of nose drops or a liquid spray, such as by means of a plastic bottle atomizer or metered-dose inhaler. Typical of atomizers are the Mistometer (Wintrop) and Medihaler (Riker).

Drops, such as eye drops or nose drops, may be formulated with an aqueous or nonaqueous base also comprising one or more dispersing agents, solubilizing agents or suspending agents. Liquid sprays are conveniently delivered from pressurized packs. Drops can be delivered by means of a simple eye dropper-capped bottle or by means of a plastic bottle adapted to deliver liquid contents by drop by means of a specially shaped closure.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

The dosage formulations provided by this invention may contain the therapeutic compounds of the invention, either alone or in combination with other therapeutically active ingredients, and pharmaceutically acceptable inert excipients. The term 'pharmaceutically acceptable inert excipients' includes at least one of diluents, binders, lubricants/glidants, coloring agents and release modifying polymers.

Suitable antioxidants may be selected from amongst one or more pharmaceutically acceptable antioxidants known in the art. Examples of pharmaceutically acceptable antioxidants include butylated hydroxyanisole (BHA), sodium ascorbate, butylated hydroxytoluene (BHT), sodium sulfite, citric acid, malic acid and ascorbic acid. The antioxidants may be present in the dosage formulations of the present invention at a concentration between about 0.001% to about 5%, by weight, of the dosage formulation.

Suitable chelating agents may be selected from amongst one or more chelating agents known in the art. Examples of suitable chelating agents include ethylenediaminetetraacetic acid (EDTA), edetic acid, citric acid and combinations thereof. The chelating agents may be present in a concentration between about 0.001% and about 5%, by weight, of the dosage formulation.

The dosage form may include one or more diluents such as lactose, sugar, cornstarch, modified cornstarch, mannitol, sorbitol, and/or cellulose derivatives such as wood cellulose and microcrystalline cellulose, typically in an amount within the range of from about 20% to about 80%, by weight.

The dosage form may include one or more binders in an amount of up to about 60% w/w. Examples of suitable binders include methyl cellulose, hydroxypropyl cellulose, hydroxypropylmethyl cellulose, polyvinyl pyrrolidone, eudragits, ethyl cellulose, gelatin, gum arabic, polyvinyl alcohol, pullulan, carbomer, pregelatinized starch, agar, tragacanth, sodium alginate, microcrystalline cellulose and the like.

Examples of suitable disintegrants include sodium starch glycolate, croscarmellose sodium, crospovidone, low substituted hydroxypropyl cellulose, and the like. The concentration may vary from 0.1% to 15%, by weight, of the dosage form.

Examples of lubricants/glidants include colloidal silicon dioxide, stearic acid, magnesium stearate, calcium stearate, talc, hydrogenated castor oil, sucrose esters of fatty acid, microcrystalline wax, yellow beeswax, white beeswax, and the like. The concentration may vary from 0.1% to 15%, by weight, of the dosage form.

Release modifying polymers may be used to form extended release formulations containing the therapeutic compounds of the invention. The release modifying polymers may be either water-soluble polymers, or water insoluble polymers. Examples of water-soluble polymers include polyvinylpyrrolidone, hydroxy propylcellulose, hydroxypropyl methylcellulose, vinyl acetate copolymers, polyethylene oxide, polysaccharides (such as alginate, xanthan gum, etc.), methylcellulose and mixtures thereof. Examples of water-insoluble polymers include acrylates such as methacrylates, acrylic acid copolymers; cellulose derivatives such as ethylcellulose or cellulose acetate; polyethylene, and high molecular weight polyvinyl alcohols.

Another embodiment of the invention relates to the use of any of the prodrug compounds or compositions described herein in the preparation of a medicament for the treatment of a thioesterase deficiency disorder.

Also encompassed by the present invention are methods for screening potential therapeutic agents that may prevent, treat or inhibit the formation of a thioesterase deficiency disorder, by functionally mimicking a thioesterase enzymatic activity comprising: (a) combining an s-acylated protein having a thioester linkage and a potential therapeutic compound under conditions in which they interact, and; (b) monitoring the cleavage of the thioester linkage; wherein a potential therapeutic compound is selected for further study when it mimics the thioesterase enzymatic activity compared to a control sample to which no potential therapeutic compound has been added. In one embodiment, the potential therapeutic compound is selected from the group consisting of a pharmaceutical agent, a cytokine, a small molecule drug, a cell-permeable small molecule drug, a hormone, a combination of interleukins, a lectin, a bispecific antibody, and a peptide mimetic. In another embodiment, the potential therapeutic compound is a compound of Table 1 or an analog or derivative thereof.

Another embodiment of the invention relates to the use of any of the compounds or compositions of the invention in the preparation of a medicament for the inhibition of a thioesterase deficiency disorder in a mammal.

Each publication or patent cited herein is incorporated herein by reference in its entirety.

Although the invention has been described in conjunction with specific embodiments thereof, the foregoing description is intended to illustrate and not limit the scope of the invention. Other aspects, advantages, and modifications within the scope of the invention will be apparent to those skilled in the art to which the invention pertains.

EXAMPLES

Unless otherwise indicated, the practice of the present invention can employ conventional techniques known to those of skill of the arts of the pharmaceutical industry and the like. To the extent such techniques are not described fully herein, one can find ample reference to them in the scientific literature.

Materials and Methodology

Cell Culture

PPT1-deficient immortalized INCL lymphoblast-cultures were obtained from the laboratory of the late Dr. Krystina E. Wisniewski. PPT 1-deficient fibroblasts were derived from skin biopsy sample from an INCL patient admitted to a clinical protocol (#01-CH-0086), approved by the Institutional Review Board (IRB) of the NICHD, NIH. This patient was homozygous for one of the most lethal PPT1 gene mutations (R122W). A list of cell lines used and the PPT1-mutations they carried have been provided in Table 2, below. Fibroblasts were cultured in DMEM supplemented with 10% heat inactivated fetal bovine serum (FBS), 2 mM glutamine, 100 U/ml penicillin and streptomycin at 37° C. in humidified atmosphere with 5% $CO_2$. INCL and normal lymphoblasts were cultured in RPMI supplemented with 16% FBS at 37° C. in humidified atmosphere with 5% $CO_2$.

TABLE 2

| PPT1 deficient cells | | |
|---|---|---|
| Cell Line | PPT1-Mutation | |
| Lymphoblasts | | |
| 1. C11568 | Missense | A364T (R122W) |
| | Missense | G541A (V181M) |
| 2. C12275 | Missense | G353A (G118D) |
| | Nonsense | C451T (R151X) |
| 3. C11796 | Nonsense | C451T (R151X) |
| | Nonsense | C451T (R151X) |
| 4. C10949 | Nonsense | C490T (R161X) |
| | Nonsense | C490T (R161X) |
| 5. C1045LT | Nonsense | C451T (R151X) |
| | Nonsense | C451T (R151X) |
| 6. C7142L | Nonsense | C451T (R151X) |
| | Missense | G541A (V181M) |
| 7. C10320LT | Nonsense | C451T (R151X) |
| | Missense | G749T (G250V) |
| 8. C11560 | Missense | A223C (T75P) |
| | Nonsense | C451T (R151X) |

TABLE 2-continued

| PPT1 deficient cells | | |
|---|---|---|
| Cell Line | PPT1-Mutation | |
| 9. C12488 | Missense | A223C (T75P) |
| | Missense | A223C (T75P) |
| 10. C9955 | Normal Lymphoblasts | |
| | Fibroblasts | |
| INCL Fibroblasts | Missense | A364T (R122W) |
| | Missense | A364T (R122W) |

Animals

All animal experiments were performed according to the institutional guidelines after an animal protocol was approved by the Animal Care and Use Committee of the National Institute of Child Health and Development, National Institutes of Health. PPT1-KO mice (a gift from Dr. S. L. Hofmann, University of Texas Southwestern Medical Center at Dallas, Dallas, Tex., USA) were generated by targeted disruption of the last exon in the PPT1 gene in embryonic stem (ES) cells. These mice were subsequently backcrossed for 10 generations with wild type C57BL/6 mice in order to obtain congenic C57 background and a breeding pair was provided by Dr. Mark Sands to start the inventors' colony. Animals were housed and maintained in a pathogen-free facility. Three-month old PPT-KO mice were given NtBuHA in their drinking water (1 mM NtBuHA and 1 mM NaCl).

Transmission Electron Microscopy

Transmission electron microscopy was performed using standard methodology. Briefly, after treatment with PTC124 for 7 days, cells were fixed with 2.5% glutaraldehyde in sodium phosphate buffer and then washed with Millonig's phosphate buffer once and kept in the same buffer at 4° C. until final processing. Ultra-thin sections were then prepared and then stained with lead citrate and uranyl acetate and examined with a LEO 912 electron microscope (JFE Enterprises).

Western Blot Analysis

Western blot analysis was performed as using standard methodology. Briefly 30 μg of protein was resolved in 4-12% Bis tris gel (Invitrogen) and electro-transferred in PVDF membrane. The membranes were blocked with 5% non fat dried milk for 1 hour at room temperature and were then probed overnight with primary antibody at 4 C. After washing the blots were incubated with horseradish peroxidase conjugated secondary antibody (Santacruz Biotechnology) for 1 hour at room temperature and developed using enhanced chemiluminescences detection reagents (Pierce). Primary antibodies used in this study were caspase-3, caspase-9 (cell signaling) SOD2, catalase, β-Actin (US Biologicals).

Immunohistochemistry

The NtBuHA treated and untreated mouse brain tissues were fixed in 3.7% paraformaldehyde, embedded in paraffin and processed for histological analyses. Briefly, after being treated with xylene and then successively with different concentrations of ethanol in phosphate buffered saline (PBS) (100% to 0%), tissue sections were blocked with 5% BSA in PBS. Sections were then probed overnight with anti-synaptophysin (Abcam) and anti-GFAP followed by incubation with alexa fluor 594 conjugated anti-rabbit and anti-mouse secondary antibodies (Invitrogen). Sections were mounted with DAPI containing mounting medium and imaged using Zeiss LSM 510 Inverted Meta confocal microscope (Carl Zeiss).

Immunofluorescence Analysis

Immunofluoresence analysis was performed according to the method of Tanida et al. Briefly cells were grown in 2-chamber slide (Lab-Tek) and fixed with 4% paraformaldehyde for 10 min at room temperature. Cells were blocked with 2% BSA and 5% serum in PBS for 1 h at room temperature and then probed overnight with primary antibody at 4 C, followed by incubation with secondary antibodies at room temperature for 1 h. Primary antibodies used were anti-Saposin A and D. Secondary antibodies used are Alexa fluor 488 conjugated anti-rabbit, alexa fluor conjugated 594 anti-mouse (Invitrogen). Nuclei were stained with DAPI (Sigma-Aldrich). Fluorescence was visualized using Zeiss LSM 510 Inverted Meta confocal microscope (Carl Zeiss), and the image obtained was processed and analyzed with the LSM image software (Carl Zeiss).

Cellular Apoptosis Detection

To evaluate whether NtBuHA protects against oxidative stress-induced apoptosis in INCL lymphoblasts the cells were treated with 1 mM NtBuHA for 12 hours and then incubated with 500 µM $H_2O_2$ for 3 hours in presence or absence of NtBuHA (1 mM). Untreated INCL lymphoblasts were also treated with $H_2O_2$ for 3 hours. For the detection of apoptosis the cells were stained with annexin V using Apoptosis detection kit (Biovision) and analyzed by FACS (Guava EasyCyte Mini System, Millipore).

Palmitoylated Protein Isolation

Palmitoylated proteins were identified by acyl-biotinyl exchange protocol as described by Roth et al (2006) with minor modifications. Briefly cells were lysed with RIPA buffer (Pierce) and incubated overnight with 10 mM N-ethylmalemide (NEM, Pierce) and 1× protease inhibitor cocktail (PI, Pierce) at 4° C. with gentle mixing. The next day, NEM was removed by three sequential precipitation by the chloroform-methanol (CM) method described previously (Wessel and Flugge, 1984. Following third precipitation, the protein was divided into two parts. One part was treated with 1 M hydroxylamine (Sigma) pH 7.4 (freshly prepared), 1 mM BMCC-biotin (Pierce), 0.2% Triton X-100 (Sigma), and 1×PI and the other part was treated with similar mixture without hydroxylamine for 1 h at room temperature. The protein was then precipitated by CM method and treated with 200 µM BMCC-biotin, 0.2% Triton X-100, and 1×PI at room temperature 25° C. for 1 hour. HPDP-biotin was then removed by three sequential CM precipitations. Following the third precipitation, protein was dissolved in SDS-PAGE loading buffer and boiled for 5 min. The sample was then subjected to Western blot analysis with avidin-HRP conjugate.

Transmission Electron Microsocopy

Transmission electron microsocopy (TEM) of INCL lymphoblasts and fibroblasts was performed. Briefly, cells were first treated with 250 µM NtBuHA for 3 weeks. Medium was replaced with fresh 250 µM of NtBuHA at every 72 hours. After treatment, cells were fixed with 2.5% glutaraldehyde in sodium phosphate buffer, washed three times with Millonig's phosphate buffer and stained with 2.5% uranyl acetate. Ultra-thin sections were then prepared using AO Reichert Ultracut ultramicrotome, stained with lead citrate and examined by using Zeiss EM10 CA.

Cortical tissue sections were prepared from wild-type mice and untreated- as well as NtBuHA-treated PPT1-KO littermates. Cortical tissues (approximately 1 mm³) were dissected from those animals, fixed in 2.5% glutaradlehyde in 0.1M sodium cacodylate buffer, pH 7.4 followed by three washing in 0.1 M sodium cacodylate buffer at room temperature. Tissues were then post-fixed with 1% osmium tetroxide, dehydrated by sequential treatment of 50%, 70%, 90% and 100% ethanol and treated with Spurr's resin/ethanol using a variable wattage Pelco BioWave Pro microwave oven. Cortical tissues were embedded and polymerized in 100% resin for 18 hours at 70° C. Tissue sections (50 nm thick) were prepared using Reichert-Jung Ultracut-E ultramicrotome and collected on LuxFilm grids (Ted Pella, Inc.) of 30 nm film thickness. The grids were then post-stained with uranyl acetate and lead citrate and examined in a FEI Tecnai G2 transmission electron microscope operating at 80 kV.

Real Time Polymerase Chain Reaction

Real time polymerase chain reaction (RT PCR) was performed using standard protocols.

Motor Coordination Test

Motor coordination of the untreated- and NtBuHA-treated PPT1-KO mice was assessed using Rotarod) (UGO Basile, Italy) at three different speeds (4, 8 and 12 rpm). In all these speeds the direction of rotation was reversed every 15 seconds. Animals were trained twice at all speed settings for 1 minute each for 3 days. Animals were then given a rest for 1 minute between two trials. Rotarod experiments were performed for at least 60 seconds on day 4 and the amount of time a mouse was on the rotarod before falling from the rotating rod was recorded.

Statistical Analysis

All data were expressed as the mean of at least three experiments ±SD. Results were analyzed using one way ANOVA and $p<0.05$ was considered significant.

Example 1

This Example demonstrates that derivatives of hydroxylamine (HA) are able to cleave the thioester linkage in [$^{14}$C]palmitoyl-CoA in vitro.

It has been reported that thioester linkages in s-acylated proteins are labile, and that compounds having nucleophilic properties are able to disrupt such linkages. Thus, the ability of derivatives of hydroxylamine to disrupt thioester linkages in s-acylated proteins was tested. Twelve HA-derivatives, described in Table 1, were screened for their ability to cleave thioester linkage in [$^{14}$C]palmitoyl-CoA (a model thioester substrate of PPT1), mediating the release of free [$^{14}$C] palmitic acid, a process depicted in FIG. 2. The parent compound, HA, as well as recombinant human PPT1, served as positive controls. [$^{14}$C]-palmitoyl-CoA was incubated for 1 hour with each of the HA derivatives and the reaction mixture was resolved by thin layer chromatography (TLC) followed by autoradiography. The free [$^{14}$C]-palmitate bands were visible and quantitated by densitometric analysis of the bands. The results of this study demonstrated that all twelve hydroxylamine derivatives hydrolyze the thioester linkage in [$^{14}$C]palmitoyl-CoA, as shown in FIG. 3. These results suggest that HA-derivatives are capable of efficiently cleaving the thioester linkage in a model substrate of PPT1.

Example 2

This example demonstrates that ten HA-derivatives did not adversely affect the viability of cultured cells from INCL patients.

Ten out of the twelve HA-derivative compounds listed in Table 1 were tested to determine whether they adversely affected the viability of cultured cells from INCL patients. Two derivatives from Table 1, namely, N,N-dibenzylhydroxylamine and N-tert-Butyl-O-[1-[4-(chloromethyl)phenyl]ethyl]-N-(2-methyl-1-phenylpropyl)hydroxylamine, were not tested because they were insoluble in tissue culture media. Briefly, following treatment with HA-derivatives INCL cells were incubated with Thiazolyl Blue Tetrazolium Blue (MTT) for 4 hours at 37° C. Formazan crystals thus formed were dissolved in acidified isopropanol and absorption was measured at 570 nm. Viability was expressed as percent of untreated control. As illustrated in FIG. 4A-C, the results showed that all ten compounds except N-Benzoyl-N-phenyl hydroxylamine are non-toxic up to a concentration of 1 mM as there was no evidence for any adverse effect that decreased the viability of these cells.

Example 3

This Example demonstrates that three derivatives of hydroxylamine (HA) cleave the thioester linkage in [$^{14}$C] palmitoyl-CoA in a time- and dose-dependent manner.

To determine whether hydrolysis of the thioester linkage by hydroxylamine derivatives, namely N-t-butyl hydroxylamine (NtBuHA), benzyl-HA, and methyl-HA, is dose dependent, a fixed amount of [$^{14}$C]palmitoyl-CoA was incubated with varying concentrations of each of these three derivatives, and the production of [$^{14}$C]palmitate measured. To determine whether hydrolysis of the thioester linkage by the hydroxylamine derivatives is also time-dependent, a fixed amount of [$^{14}$C]palmitoyl-CoA was incubated with each of the three derivatives, and the production of [$^{14}$C] palmitate measured at various times during incubation. The results of this study demonstrated that all three of the hydroxylamine derivatives tested cleaved the thioester linkage in a dose-dependent and time-dependent manner. FIGS. 5 A and B shows the results obtained using NtBuHA.

Example 4

This Example demonstrates that derivatives of hydroxylamine (HA) are non-toxic with respect to cultured INCL fibroblasts.

Figure 6:
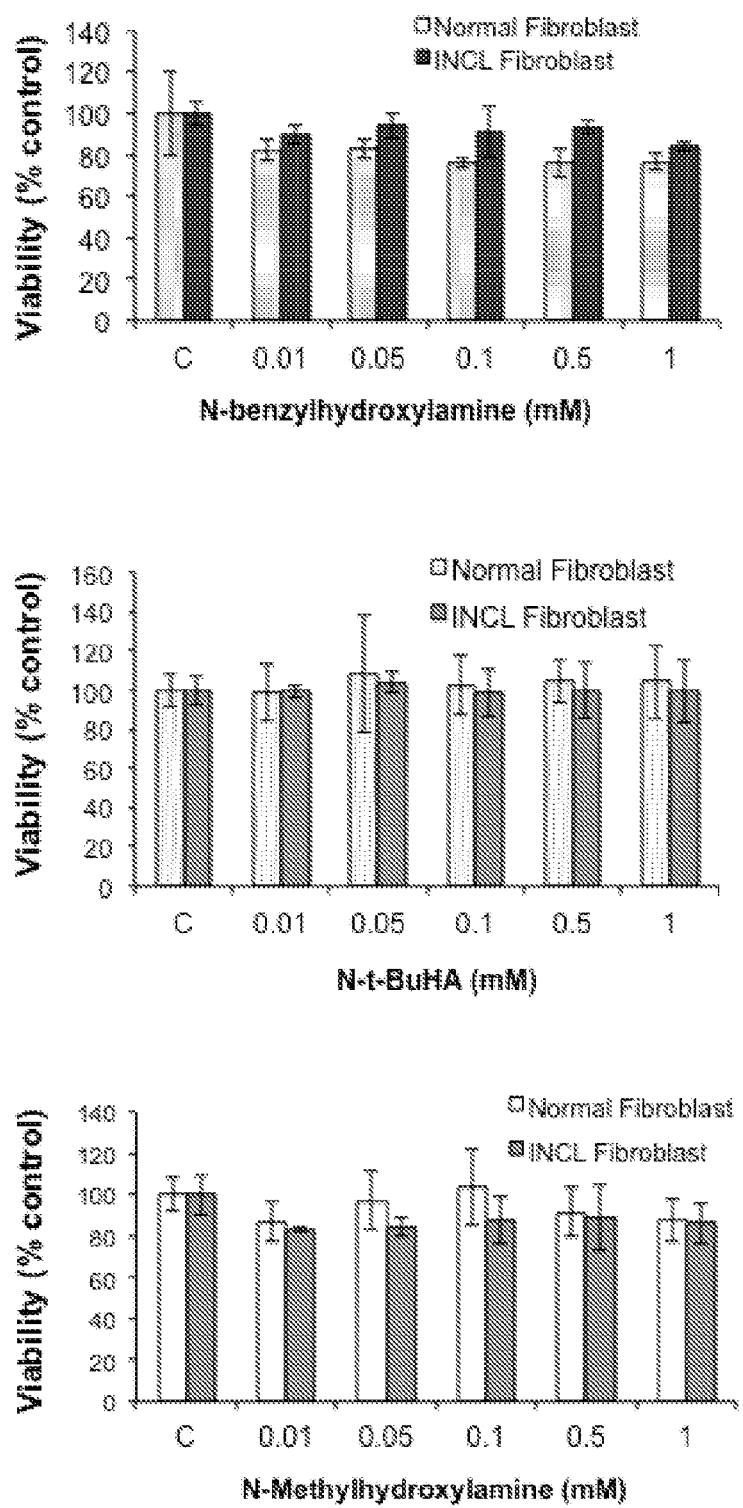
FIG. 6 charts the viability, as a percentage of untreated control, of INCL fibroblasts following treatment with different amounts of three HA-derivatives.

Before further testing the ability of hydroxylamine derivatives to cleave thioester bonds in s-acylated proteins, the potential toxicity of these derivatives was tested in cultured cells. Briefly, normal fibroblasts (GM 00498) were obtained from the Coriell Institute of Medical Research, USA. PPT1-deficient INCL fibroblasts were isolated from skin biopsy samples of INCL patients admitted to an ongoing clinical protocol (#01-CH-0086) approved by the Institutional Review Board (IRB) of the National Institute of Child Health and Human Development (NICHD) at the National Institute of Health (NIH). The fibroblasts were cultured in Dulbecco's Modified eagle medium (DMEM))(GIBCO®), supplemented with 10% heat inactivated fetal bovine serum (FBS), 2 mM glutamine, and 100 U/ml penicillin and streptomycin, at 37 C in humidified atmosphere containing 5% $CO_2$. Semi-confluent cells were harvested with 0.025% trypsin and 0.52 mM ethylenediaminetetraacetic acid (EDTA) and re-plated at a density of 5×10$^5$ cells/well in a 6-well plate. The fibroblasts were cultured in the presence or absence of varying concentrations of each of the HA-derivatives for 48 hours, after which the viability of the cells was determined using the MTT-Cell Viability Assay by T. Mossman, (Rapid colorimetric assay for cellular growth and survival. J. Immunol. Method. 65 (1983) 55-63). The results of this study, which are shown in FIG. 6, demonstrated that the three hydroxylamine derivatives are non-toxic to cultured fibroblasts.

Example 5

This Example demonstrates the ability of NtBuHA to hydrolyze thioester linkages in S-acylated proteins in cultured INCL lymphoblasts, and to mediate depletion of lipid-extractable [$^{35}$S]cysteine thioesters from these cells.

It has been demonstrated that not only is NtBuHA non-toxic, but that it is also a potent antioxidant. Thus, this derivative was chosen for more extensive study of its ability to hydrolyze S-acetylated proteins, and to deplete lipid-extractable [$^{35}$S]cysteine thioesters from fibroblasts and lymphoblasts. INCL fibroblasts were obtained and cultured as described in Example 4. The cells were then labeled with [$^{35}$S]cysteine. Briefly, following incubation for six hours in medium lacking serum and cysteine/cystine, the cells were washed and then re-cultured for varying lengths of time in medium containing NtBuHA, with a change of medium every 12 hours. As controls, [$^{35}$S]cysteine-labeled cells were cultured in drug-free medium as well as medium containing 1M HA. Following incubation, cells were washed twice with cold PBS and then centrifuged at 2,250 g at 4° C. for 5 minutes. Lipid thioesters were then extracted from the cells and subject to analysis by high-performance thin layer chromatography. Briefly, the extracted fatty acyl esters were dissolved in chloroform:methanol (1:1) and an aliquot applied to a TLC plate and resolved using a mixture of chloroform:methanol:water (65:25:4). The plates were then dried and autoradiographs obtained.

Figure 7:
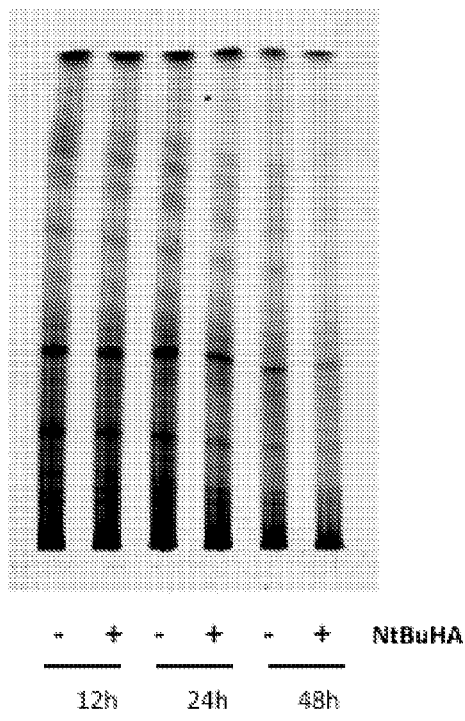
FIG. 7 depicts the densitometric analysis of [$^{35}$S]cysteine-thioester compounds of NtBuHA-treated INCL cells (labeled "+") and untreated control INCL cells (labeled "−"), at 12 hours, 24 hours, and 48 hours after testing.

The results of this study demonstrated that compared with untreated control cells, treatment with NtBuHA for 24 and 48 hours yielded [$^{35}$S]cysteine-labeled lipid extractable thioester compounds of significantly reduced intensity, as shown in FIG. 7.

The ability of NtBuHA to deplete [$^{35}$S]cysteine-thioester containing compounds was tested using [$^{35}$S]cysteine-labeled, immortalized lymphoblasts. Although the cells were obtained from patients who were PPT-deficient due to inactivating mutations in PPT1, they had been clinically diagnosed to have either infantile (INCL; n=3), late infantile (LINCL; n=3) or juvenile (JNCL; n=3) forms of NCL. The cells were labeled and then incubated in medium containing NtBuHA for 48 hours. Following incubation, the lipid esters were extracted and resolved. As shown in FIG. 8, the results demonstrated a clear reduction in the intensity of the [$^{35}$S] cysteine-labeled lipid bands in every cell line treated with NtBuHA, when compared with lipid bands from untreated cells. As expected, the normal control cells did not show abnormal accumulation of [$^{35}$S]cysteine-labeled lipid bands. These results demonstrate that treatment of cells with NtBuHA results in hydrolysis of thioester linkages in S-acylated proteins.

Example 6

This Example demonstrates that NtBuHA treatment depletes granular osmiophilic deposits (GRODs) in cultured PPT1-deficient cells.

Figure 9:
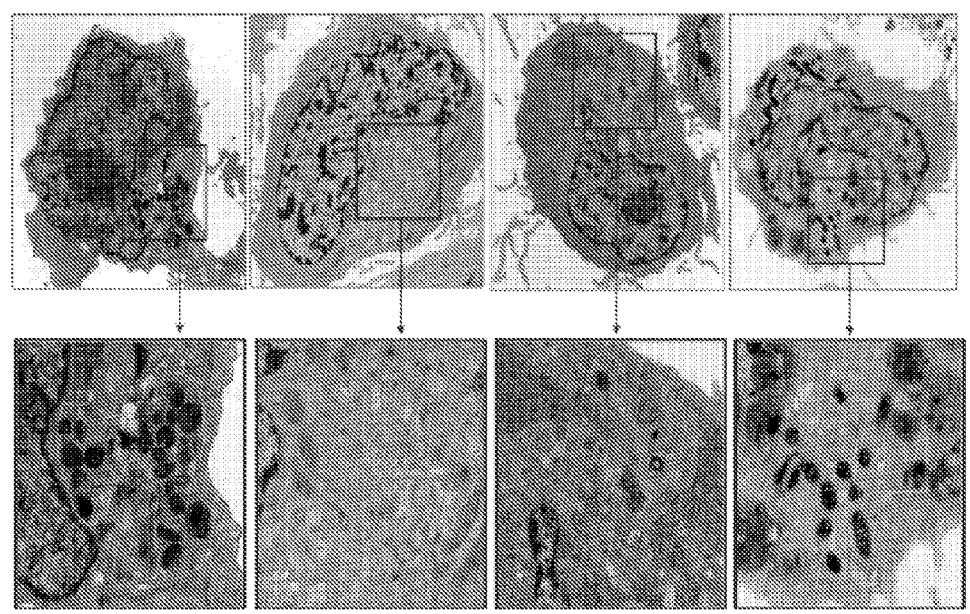
FIG. 9A-D shows TEM analysis (and magnified insets) of GRODs in untreated control INCL lymphoblasts (9A), NtBuHA-treated INCL lymphoblasts (9B and 9C), and in NtBuHA-treated lymphoblasts three weeks after treatment was withdrawn.
Figure 10:
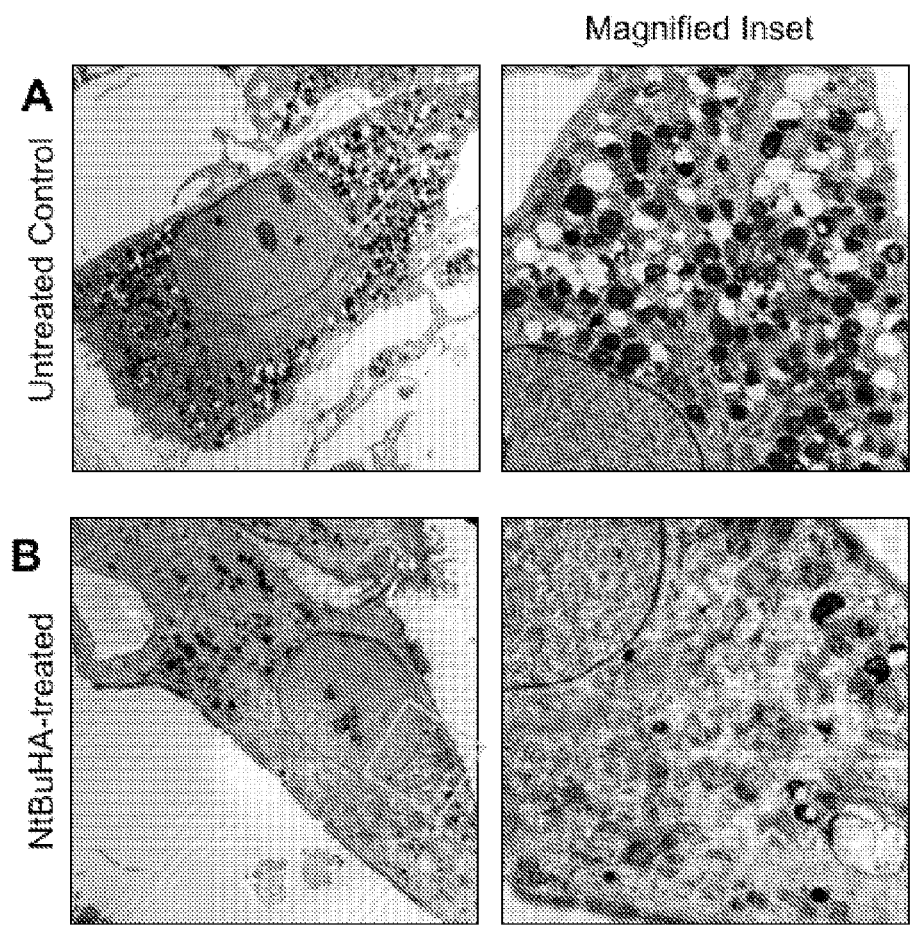
FIG. 10 shows TEM analysis (and magnified insets) of GRODs in untreated control INCL fibroblasts (10A) and in NtBuHA-treated INCL fibroblasts (10B).

It has been demonstrated that there is a physical correlation between ceroid accumulation and the presence of high concentrations of GRODs in the cells of INCL patients. Since experiments revealed that NtBuHA treatment of PPT1-deficient cells from INCL patients results in the depletion of ceroids, it was hypothesized that NtBuHA treatment of such cells would also result in depletion of GRODs, which are detectable by TEM. Accordingly, untreated- and NtBuHA-treated cultured INCL lymphoblasts were analyzed using TEM. The results showed that compared with the untreated controls, FIG. 9A, the NtBuHA-treated cells contained either no GRODs, FIG. 9B, or a substantially reduced number of GRODs that were considerably smaller in size, FIG. 9C. Similar experiments were conducted using cultured INCL patient fibroblasts, which showed that while the untreated fibroblasts contained numerous large highly dense GRODs, as shown in FIG. 10A, the NtBuHA-treated cells had significantly lower number of GRODs with markedly reduced size and density, as in FIG. 10B. These results from two different cell types from INCL patients demonstrated that NtBuHA is effective in depleting GRODs, which are characteristically found in INCL.

Example 7

This example shows that withdrawal of NtBuHA treatment promotes GROD reaccumulation in cultured INCL cells.

Figure 11:
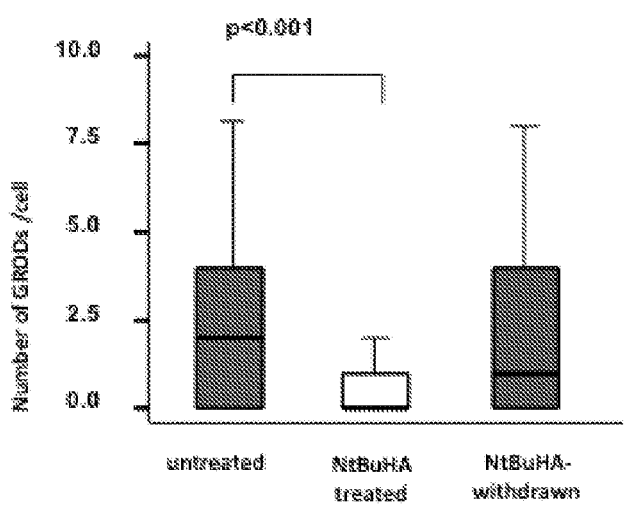
FIG. 11 charts the quantitative analysis of GRODs in untreated control INCL lymphoblasts, NtBuHA-treated INCL lymphoblasts, and in NtBuHA-treated lymphoblasts three weeks after treatment was withdrawn.

For a therapeutic agent to be effective for INCL it must not only mediate depletion of ceroid by cleaving thioester linkage in S-acylated proteins but it must also prevent re-accumulation of ceroid. To determine whether withdrawal of NtBuHA causes reaccumulation, immortalized INCL lymphoblasts that were cultured in medium containing NtBuHA for three weeks, which showed depletion of GRODs. Some of these cultures were washed with PBS and then cultured for an additional 3 weeks in medium without NtBuHA before being analyzed by TEM. The GRODS in 15-20 informative cells were counted and presented graphically, as shown in FIG. 11. The results showed that while NtBuHA-treatment reduced GRODs as expected (FIGS. 9B and 9C), its withdrawal from the culture medium caused reaccumulation (FIG. 9D).

Example 8

This experiment demonstrates the depletion of GRODs in brain tissues of NtBuHA-treated PPT 1-KO mice.

Figure 12:
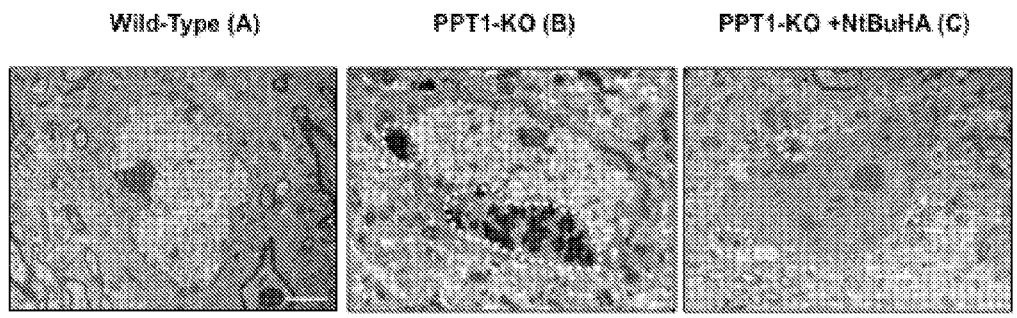
FIG. 12 shows TEM analysis of GRODs in the brain cells of wild-type mice (12A), untreated PPT1-KO mice (12B), and NtBuHA-treated PPT1-KO mice (12C).

Since the results from in vitro experiments are not always be replicable in vivo, PPT1-KO mice were obtained from Dr. S. L. Hofman at the University of Texas Southwestern Medical Center at Dallas, in Dallas, Tex. for in vivo testing. Both the knockout mice and their wild-type litter-mates (the control mice) were housed and maintained in a pathogen-free facility. To determine whether treatment with NtBuHA mediates the depletion of GRODs in vivo as well as in vitro, 3-month old PPT1-KO mice were treated with NtBuHA until they were 6 months old. Untreated age- and sex-matched PPT1-KO and wild-type mice were kept as controls. 6-month old animals were chosen because PPT1-KO mice at this age manifest signs of neurological impairment as well as pathological features of INCL including ER- and oxidative-stress, accumulation of GRODs, increased apoptosis and decreased brain volume compared with their wild-type litter-mates. At the end of this treatment period, the brain cells of the mice were examined by TEM. The results showed that while the wild-type mice had no GRODs (FIG. 12A) high levels of GRODs were clearly visible in the brain cells of untreated PPT1-KO mice (FIG. 12B). The NtBuHA-treated PPT 1-KO mice showed markedly reduced number of GRODs (FIG. 12C). Interestingly, when an infrequent GROD was detected in the brain cells of an NtBuHA-treated PPT1-KO mouse, the GRODs appeared remarkably smaller in size than those found in untreated animals (FIG. 12C). These results demonstrate that NtBuHA-treatment mediates depletion of GRODs in PPT1-KO brain cells and suggests, albeit indirectly, that this compound or its active metabolite(s) crosses the blood-brain barrier to effect this positive change. These results, taken together with those detailed in Examples 6 and 7, demonstrated that NtBuHA facilitates reduction of total ceroid load and consequent reduction in GROD levels in cultured cells from INCL patients as well as those in brain cells of PPT1-KO mice.

Example 9

This example shows that autofluorescence is diminished in the brain cells of NtBuHA-treated PPT 1-KO mice.

Figure 13:
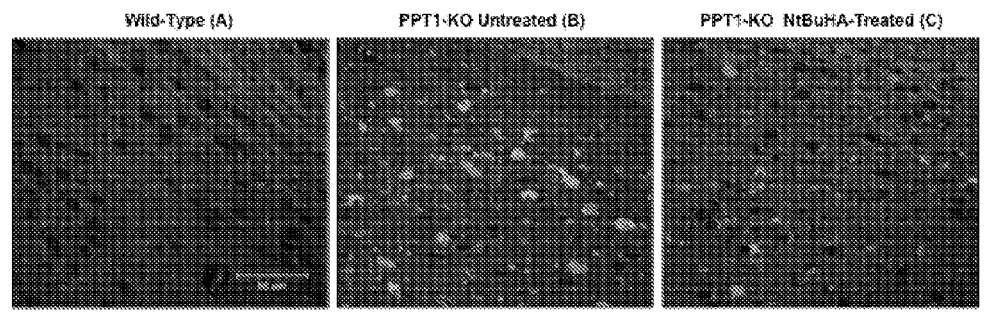
FIG. 13 shows autofluorescent analysis of the brain tissues of wild-type mice (13A), untreated PPT1-KO mice (13B), and NtBuHA-treated PPT1-KO mice (13C).

Accumulation of intracellular autofluorescent lipopigment material in the brain and other tissues is a characteristic pathological finding in INCL patients and in PPT1-KO mice. Given this, it was hypothesized that NtBuHA-mediated depletion of GRODs may also reduce the intensity of autofluorescence in brain tissues of NtBuHA-treated PPT1-KO mice. Accordingly, a comparison of the autofluorescence of brain tissues from NtBuHA-treated PPT 1-KO mice, untreated PPT 1-KO mice, and wild-type litter-mates was performed. Results showed that while the brain tissues from wild-type mice had no autofluorescence (FIG. 13A) those of the untreated PPT1-KO mice manifested intense autofluorescence (FIG. 13B). NtBuHA-treated Ppt1-KO mice had markedly reduced autofluorescence (FIG. 13C) compared with those of the untreated PPT1-KO mice. These results further confirmed that NtBuHA mediated depletion of intracellular ceroid and consequently, diminished the intensity of autofluorescence.

Example 10

This Example demonstrates that treatment of mice with NtBuHA promotes degradation of long-lived proteins.

It has been reported previously that in mice lacking Atg7, the degradation of long-lived proteins is impaired under normal and starvation conditions (Komatsu et al., 2005). PPT1-KO mice lack Atg7, which facilitates autophagosome formation. Since it appears that impairment of autophagosome-lysosome fusion in PPT1-deficient cells is due to failure of dynamic palmitoylation of Rab7, an experiment was conducted to determine whether NtBuHA treatment facilitating dynamic palmitoylation would also promote degradation of long-lived proteins in the cells of PPT 1-KO mice.

PPT1-KO mice were given drinking water containing NtBuHA. Wild-type controls were given regular water. Some mice were subjected to one day of fasting prior to harvest of cells. At the end of the treatment period, fibroblasts were obtained from both the PPT1-KO and wild-type mice and incubated with long-lived and short-lived proteins. At the end of the experiment, the percentage of protein degradation was calculated. The results showed that the amount of total proteins decreased following one day of fasting in the fibroblasts of the control mice. In contrast, fasting did not significantly decrease the amount of total cellular proteins in the cells of the PPT1-KO mice. The amount of total proteins in the cells of the PPT1-KO mice was higher compared to normal control cells. These results indicated that the decrease of total proteins is dependent on autophagosome-lysosome fusion and that it was impaired in the cells of PPT1-KO mice.

Example 11

This example shows that NtBuHA suppresses endoplasmic reticulum and oxidative-stress in the brain cells of PPT 1-KO mice.

Figure 14:
FIG. 14 shows Western blot analysis of the brain lysates from wild-type mice (labeled "WT"), untreated PPT1-KO mice (labeled "KO"), and ntBuHA-treated PPT1-KO mice (labeled "ntBuHA") for ER-stress markers Grp-78, Grp-94, and ATF6 (FIG. 14A) as well SOD2 and catalase (FIG. 14B).

It has previously reported that endoplasmic reticulum (ER-) and oxidative-stress contribute to neuropathology in INCL patients. Recently, it has been demonstrated also that mutations in the CLN3 gene that underlie juvenile neuronal ceroid lipofuscinosis (JNCL or Batten disease) also cause oxidative stress leading to neurodegeneration in Drosophila flies. Therefore, the inventors sought to determine whether NtBuHA-treatment of PPT1-KO mice ameliorate the ER- and oxidative-stress in brain tissues of these mice. Accordingly, the levels of ER-stress markers Grp-78, Grp-94 and ATF6 were determined by Western blot analysis of brain lysates. The results showed that the levels of all three ER-stress markers were reduced in brain tissues of NtBuHA-treated PPT1-KO mice (FIG. 14A). Western blot analysis of brain lysates from NtBuHA-treated and untreated PPT1-KO mice was also performed to determine the levels of superoxide dismutase-2 (SOD2) and catalase, which increases with elevated oxidative-stress. Results showed that compared with untreated PPT1-KO mice, NtBuHA-treatment significantly reduced the levels of both SOD2 and catalase (FIG. 14B). Taken together, these results demonstrated that NtBuHA-treatment reduces both ER- and oxidative stress levels in the brain tissues of PPT1-KO mice.

Example 12

Figure 15:
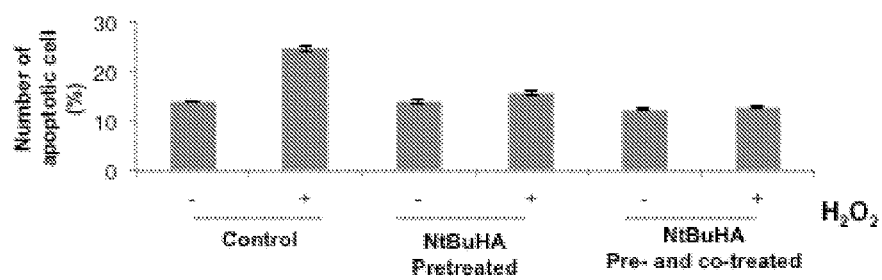
FIG. 15 charts the number of apoptotic cells (by percentage) after FACS analysis of $H_2O_2$ incubated (labeled "+") and non-$H_2O_2$ incubated (labeled "−") untreated INCL lymphoblasts (labeled "control"), NtBuHA-pretreated INCL lymphoblasts, and NtBuHA pre- and co-treated INCL lymphoblasts.

This example shows suppression of apoptosis in NtBuHA-treated cultured cells from INCL patients Reports have indicated that PPT1 plays critical roles in protecting neuroblastoma cells against apoptosis. Moreover, in these cells antisense-mediated inhibition of PPT1 leads to increased apoptosis. Consistent with these results, an increased rate of apoptosis in the brain biopsy material and in cultured immortalized lymphoblasts from INCL patients have been reported. In addition, increased neuronal apoptosis in the brain of PPT1-KO mice has also been reported. Together, these results at least in part provided an explanation for the rapidly progressive cerebral atrophy in INCL patients. Thus, the inventors sought to determine whether the NtBuHA-treatment protects cultured immortalized INCL lymphoblasts from oxidative-stress mediated apoptosis. Cultured lymphoblasts from INCL patients were chosen because PPT1 is expressed in all tissues and PPT 1-deficiency in cultured lymphoblasts and fibroblasts from INCL patients show virtually identical pathological changes (accumulation of ceroid, GRODs and increased apoptosis) as are found in postmortem neuronal tissues from such patients. Accordingly, INCL lymphoblasts were pretreated with NtBuHA for 12 hours and then incubated with hydrogen peroxide in the presence or absence of NtBuHA for 3 hours. Untreated INCL cells were also exposed, to the same concentration of hydrogen peroxide for same amount of time. Apoptosis of the $H_2O_2$-treated cells was then quantitated by florescence activated cell sorting (FACS) analysis. The results, charted in FIG. 15, showed that while treatment of INCL lymphoblasts with $H_2O_2$ in the absence of NtBuHA increased apoptosis the $H_2O_2$-induced oxidative-stress in INCL lymphoblasts pretreated with NtBuHA failed to induce apoptosis above the base level. Similarly cells that were pretreated with NtBuHA and incubated with $H_2O_2$ in presence of NtBuHA (co-treated) also showed no alteration in apoptosis above the base level in these cells. These results showed that NtBuHA protects cultured INCL lymphoblasts from oxidative-stress mediated apoptosis.

Example 13

Figure 16:
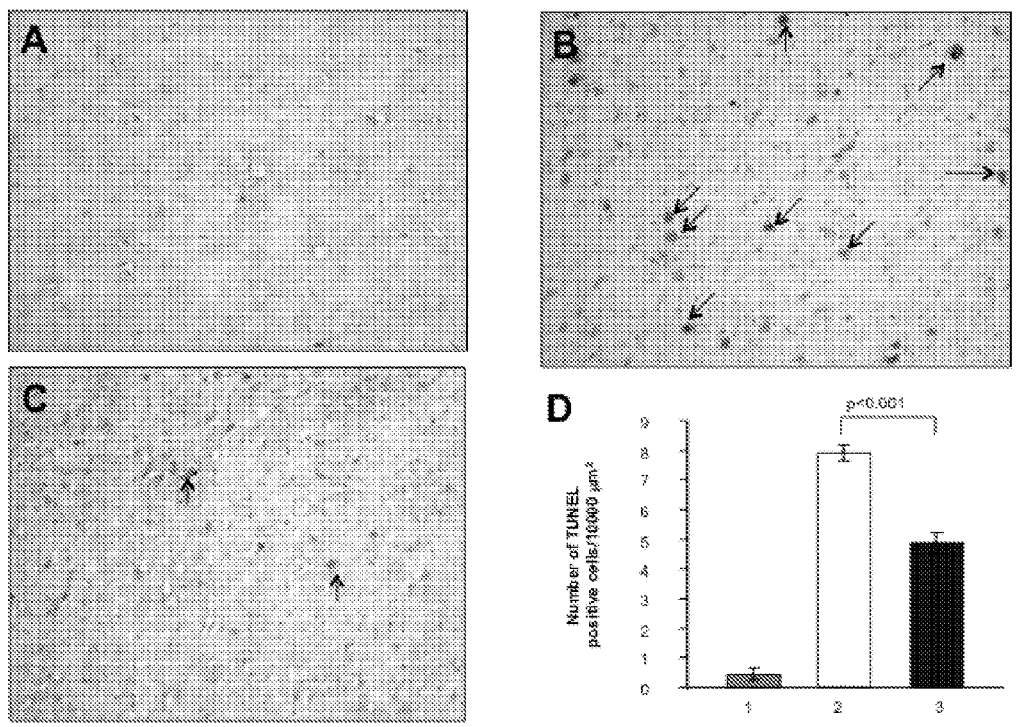
FIG. 16A-C depicts (TUNEL) assays conducted using cortical tissue sections from wild-type mice (16A), untreated PPT1-KO mice, and NtBuHA-treated PPT1-KO mice (16C) to determine apoptosis, with arrows indicating apoptotic cells.
FIG. 16D charts the quantitative analysis of this TUNEL assay of apoptotic cells, wherein cortical tissues of wild-type mice are labeled "1," untreated PPT1-KO mice are labeled "2," and NtBuHA-treated PPT 1-KO mice are labeled "3."
Figure 17:
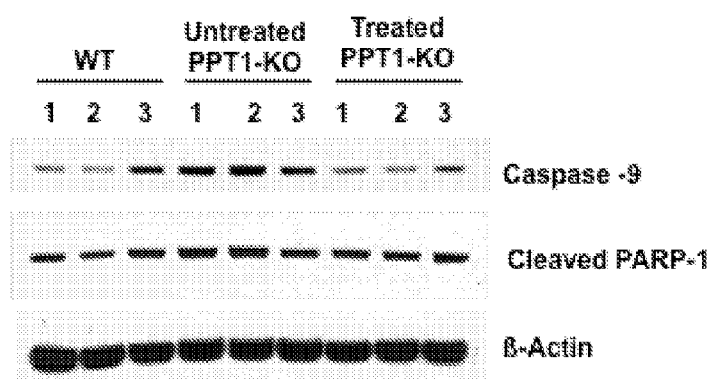
FIG. 17 shows Western blot analysis of caspase-9 and cleaved PARP-1 cortical tissue of wild-type, untreated and NtBuHA-treated PPT1-KO mice showed a marked reduction in level
Figure 18:
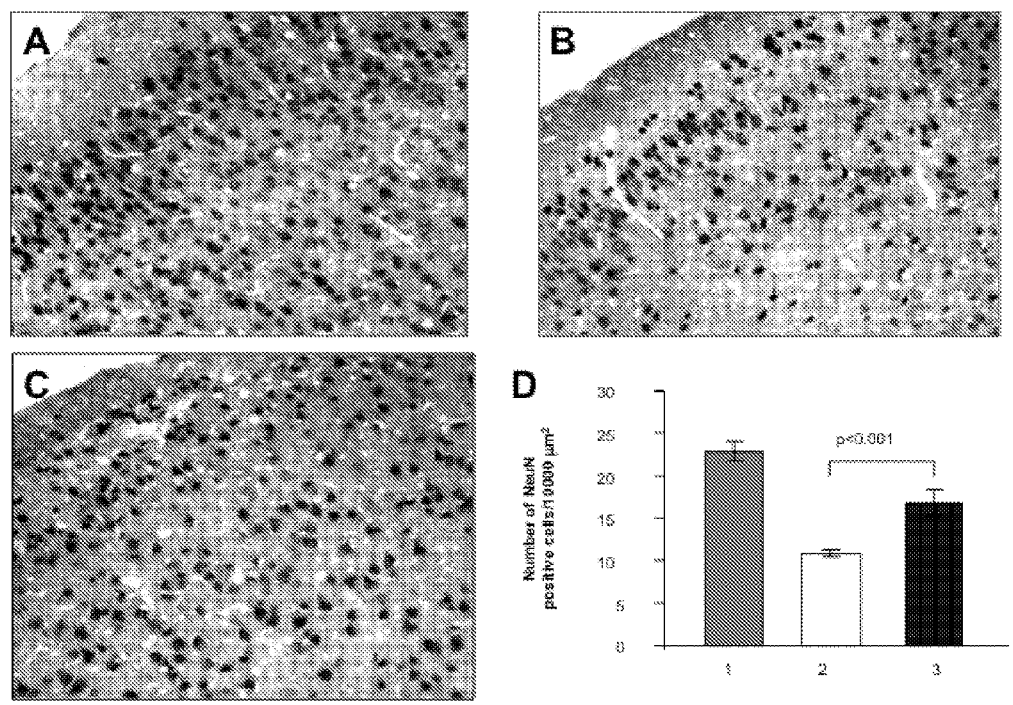
FIG. 18 depicts an immunohistochemical analyses of cortical tissue sections from wild-type (18A), untreated-PPT1-KO (18B), and NtBuHA-treated PPT1-KO (18C) mice was performed using antibodies against a neuronal marker, NeuN.

This example shows that NtBuHA reduces the level of apoptosis in Ppt1-KO mouse brain cells It has been reported that postmortem brain tissues from INCL patients as well as those from PPT1-KO mice manifest high levels of oxidative stress, which induces neuronal apoptosis contributing to neuropathology. Since the results of the testing described in Example 12 showed that NtBuHA reduces the level of apoptosis in cultured cells from INCL patients, the inventors sought to determine whether this treatment also reduces apoptosis in the brain of PPT 1-KO mice. Accordingly, a terminal deoxynucleotidyl transferase dUTP nick end labeling (TUNEL) assay was performed using cortical tissue sections from wild-type, untreated PPT1-KO and NtBuHA-treated PPT1-KO mice to determine the level of apoptosis. A visual assessment (FIGS. 16A-C) and quantitative analysis (D) showed that the wild-type mouse brain cells had virtually no TUNEL-positive apoptotic cells, the brain cells of untreated PPT 1-KO mice contained numerous apoptotic cells (FIG. 16B), and the brain tissues from NtBuHA-treated PPT 1-KO mice showed appreciably lower levels of TUNEL-positive apoptotic cells than in the brain cells of the untreated PPT 1-KO mice. Furthermore, Western blot analysis of cortical tissue homogenates of wild-type, untreated and NtBuHA-treated PPT1-KO mice showed a marked reduction in caspase-9 and cleaved PARP-1 level (FIG. 17). Since elevated levels of apoptosis in the brain of PPT1-KO mice and INCL patients mediate progressive decline in number of cortical neurons, the inventors also sought to further confirm whether decreased apoptosis in NtBuHA-treated PPT1-KO mice prevented neuronal loss. Accordingly, an immunohistochemical analyses of cortical tissue sections from wild-type, untreated-PPT1-KO, and NtBuHA-treated PPT1-KO mice was performed using antibodies against a neuronal marker, NeuN. Results showed that compared with the brain of WT mice (FIG. 18A) that of the untreated-PPT1-KO mice had an appreciably reduced number of NeuN-positive cells (FIG. 18B). Remarkably, the brain sections from NtBuHA-treated PPT1-KO mice showed a modestly higher level of NeuN-positive cells (FIG. 18C). Quantitative analysis of the NeuN-positive cells in brain tissues from wild-type, untreated and NtBuHA-treated PPT1-KO mice (FIG. 18D) confirmed the visual assessment. Taken together, these results provided supporting evidence that NtBuHA-treatment had a neuroprotective effect on PPT1-KO mice.

Example 14

The ability of the HA-derivative NtBuHA to increase methemoglobin levels was tested by placing PPT1-KO mice on a diet containing NtBuHA. After three months on the diet, the level of methemoglobin in the animal's blood was measured. The results of this study are shown below in Table 3.

TABLE 3

Methemoglobin wild-type, untreated PPT1-KO, NtBuHA-treated PPT1-KO mice

| Genotype | % Methemoglobin | Mean± | SD |
| --- | --- | --- | --- |
| WT-1 | 1.6 | 1.5 | 0.310913 |
| WT-2 | 1.0 | | |
| WT-3 | 1.1 | | |
| WT-4 | 0.9 | | |
| KO-1 | 1.1 | 1.025 | 0.221736 |
| KO-2 | 1.3 | | |
| KO-3 | 0.8 | | |
| KO-4 | 0.9 | | |
| BuHA-1 | 0 | 0.45 | 0.310913 |

TABLE 3-continued

Methemoglobin wild-type, untreated PPT1-
KO, NtBuHA-treated PPT1-KO mice

| Genotype | % Methemoglobin | Mean± | SD |
|---|---|---|---|
| BuHA-2 | 0.5 | | |
| BuHA-3 | 0.7 | | |
| BuHA-4 | 0.6 | | |

The results demonstrate that NtBuHA treatment up to three months does not increase methemoglobin levels in PPT1-KO mice.

Example 15

Figure 19:
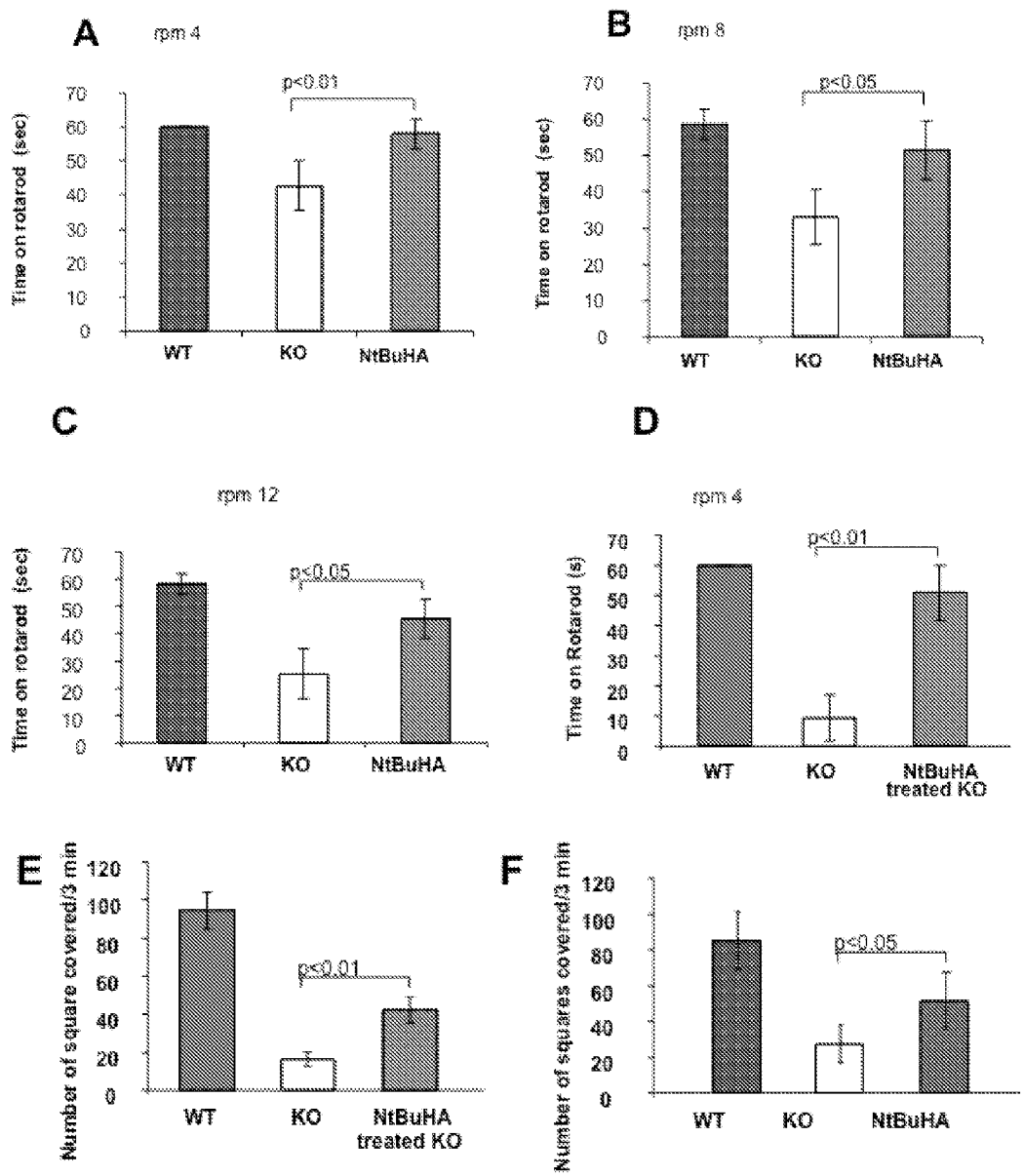
FIG. 19 charts the motor coordination of 6-month and 8-month old wild-type ("WT"), untreated-PPT 1-KO mice ("KO") and NtBuHA-treated PPT 1-KO mice ("NtBuHA") on the Rotarod Performance Test for motor coordination (FIGS. 19A-D) and the open field test exploratory behavior (FIGS. 19E-F).

This example shows that NtBuHA-treated PPT1-KO mice retain near normal motor coordination and exploratory behavior at 6- and 8-months old The natural history of INCL shows that psychomotor deterioration is one of the first signs to be recognized in patients with INCL. It has been recently demonstrated that transplantation of human neuroprogenitor stem cells into the brain of PPT1-KO mice delayed loss of motor coordination, most likely by producing PPT 1. Since NtBuHA functionally mimics PPT1, the inventors tested 6-month and 8-month old wild-type, untreated- and NtBuHA-treated PPT1-KO mice for motor coordination and exploratory behavior. The Rotarod Performance Test, which measures parameters such as riding time (seconds) and/or endurance was used to measure motor coordination. The open field test was utilized to evaluate the exploratory behavior. The results showed that NtBuHA-treated PPT1-KO mice retained near normal motor function (FIG. 19A-D) as well as exploratory behavior (FIG. 19E-F). These results suggest that NtBuHA-treatment of PPT1-KO mice prevents deterioration of motor coordination and helps maintain exploratory behavior in PPT 1-KO mice.

Example 16

This example shows that NtBuHA extends lifespan in PPT 1-KO mice.

Figure 20:
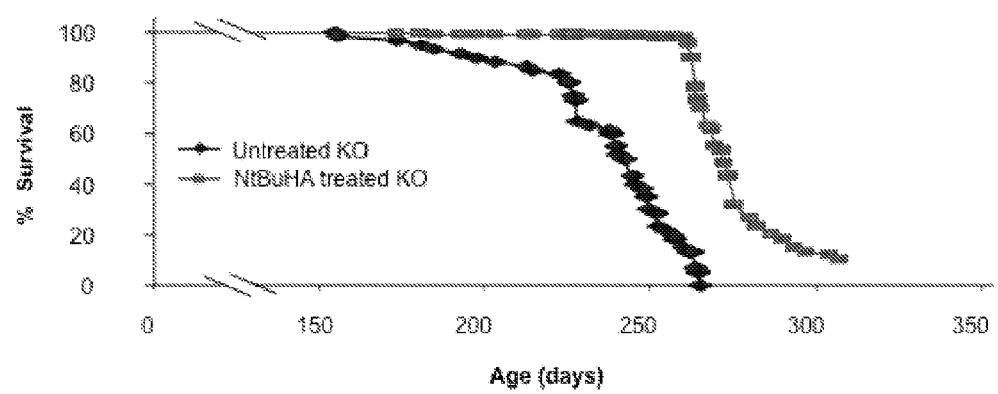
FIG. 20 compares the survival rates of untreated PPT 1-KO mice and NtBuHA-treated PPT1-KO mice by percentage surviving over a given course of time.

For this study, 3-month old PPT1-KO mice were divided into two groups. In the first group, 55 mice received no treatment (control). In the second group, 59 mice were treated with NtBuHA. The status of all mice was monitored on a daily basis. At 5.5 months after the initiation of the experiment the results showed that while 52 out of 59 mice (88%) NtBuHA-treated mice were still alive and apparently healthy whereas only 10% of the untreated mice were alive (FIG. 20). This experiment shows that NtBuHA-treatment expands lifespan in PPT1-KO mice.

The foregoing examples of the present invention have been presented for purposes of illustration and description. Furthermore, these examples are not intended to limit the invention to the form disclosed herein. Consequently, variations and modifications commensurate with the teachings of the description of the invention, and the skill or knowledge of the relevant art, are within the scope of the present invention. The specific embodiments described in the examples provided herein are intended to further explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A method of preventing, treating or ameliorating a thioesterase deficiency disorder disease selected from neuronal ceroid lipofuscinosis (NCL), infantile NCL, and juvenile NCL, comprising administering to a mammal in need of such treatment, a therapeutically effective amount of a compound that functionally mimics a thioesterase enzymatic activity selected from the group consisting of: N-t-butyl hydroxylamine (NtBUHA), N-Methylhydroxylamine, N,N-Dimethylhydroxylamine, N,N-Diethylhydroxylamine, N-Cyclohexylhydroxylamine, N,O-Bis(trimethylsilyl)hydroxylamine, N-Benzylhydroxylamine, N-Benzyloxycarbonyl), N,O-Di-Boc-hydroxylamine, N-Benzoyl-N-phenyl hydroxylamine, N,N-Dibenzylhydroxylamine, N-tert-Butyl-O-[1-[4-(chloromethyl)phenyl]ethyl]-N-(2-methyl-1-phenylpropyl)hydroxylamine, and pharmaceutically-acceptable salts thereof.

2. The method of claim 1, wherein the compound mimics palmitoyl protein thioesterase-1 enzymatic activity.

3. The method claim 1, wherein the compound is N-t-butyl hydroxylamine or a pharmaceutically-acceptable salt thereof.

4. The method of claim 1, wherein the mammal is suspected of having at least one mutation in both alleles of a gene encoding a thioesterase.

5. The method of claim 1, wherein the compound is administered to the mammal in a pharmaceutical composition.

6. The method of claim 5, wherein the pharmaceutical composition is a mono-phasic pharmaceutical composition suitable for parenteral or oral administration consisting essentially of a therapeutically-effective amount of the compound, and a pharmaceutically acceptable carrier.

7. The method of claim 1, wherein the compound is administered to the mammal in an amount from about 0.1 to about 100 mg per kilogram.

* * * * *